US012805467B2

(12) United States Patent
Carver

(10) Patent No.: US 12,805,467 B2
(45) Date of Patent: Nov. 24, 2026

(54) WHEAT VARIETY OK15MASBx7 ARS 8-29

(71) Applicant: THE BOARD OF REGENTS FOR THE OKLAHOMA AGRICULTURAL AND MECHANICAL COLLEGES, Stillwater, OK (US)

(72) Inventor: Brett F. Carver, Stillwater, OK (US)

(73) Assignee: BOARD OF REGENTS FOR THE OKLAHOMA AGRICULTURAL AND MECHANICAL COLLEGES, Stillwater, OK (US)

( * ) Notice: Subject to any disclaimer, the term of this patent is extended or adjusted under 35 U.S.C. 154(b) by 624 days.

(21) Appl. No.: 18/174,421

(22) Filed: Feb. 24, 2023

(65) Prior Publication Data

US 2024/0284849 A1 Aug. 29, 2024

(51) Int. Cl.
*A01H 5/10* (2018.01)
*A01H 6/46* (2018.01)

(52) U.S. Cl.
CPC ............. *A01H 6/4678* (2018.05); *A01H 5/10* (2013.01)

(58) Field of Classification Search
None
See application file for complete search history.

(56) References Cited

U.S. PATENT DOCUMENTS 8,309,830 B2 * 11/2012 Ward ....................... A01H 5/10 800/300

OTHER PUBLICATIONS

Larkin et al. Heritable somaclonal variation in wheat. Theor Appl Genet. Mar. 1984;67(5):443-55. (Year: 1984).*
Cooper. 2014, dissertation entitled Improving End-use Quality in Hard Winter Wheat Through Glutenin Allele Combinations and Genomic Selection, Colorado State University, Department of Soil and Crop Sciences. (Year: 2014).*
Carver, B., "WQC HWW Review, 2021 Crop[Powerpoint]", Feb. 24, 2022, 10 pages.
Edelson, J., Oklahoma Agricultural Experiment Station (OAES), "Doublestop CL Plus," Certificate and Application for Plant Variety Protection, PVPO No. 201400228, filed Mar. 5, 2014, 21 pages.
Edelson, J., Oklahoma Agricultural Experiment Station (OAES), "Gallagher," Certificate and Application for Plant Variety Protection, PVPO No. 201300134, filed Feb. 6, 2013, 17 pages.
Haley, S., Colorado Wheat Research Foundation, "Snowmass," Certificate and Application for Plant Variety Protection, PVPO No. 201000432, filed Aug. 10, 2010, 66 pages.
Ham, G., Kansas Agricultural Experiment Station, "Jagger," Certificate and Application for Plant Variety Protection, PVPO No. 9500324, filed Sep. 25, 1995, 27 pages.
Messmer, M.J., HybriTech US, a Monsanto Company, "Ponderosa," Certificate and Application for Plant Variety Protection, PVPO No. 9300290, filed Aug. 16, 1993, 20 pages.
Metz, S., Monsanto Company, "Jagalene," Certificate and Application for Plant Variety Protection, PVPO No. 200200160, filed May 23, 2002, 14 pages.
Owens, K., Oklahoma Agricultural Experiment Station (OAES), "Butler's Gold," Certificate and Application for Plant Variety Protection, PVPO No. 202100244, filed Mar. 17, 2021, 26 pages.
Owens, K., Oklahoma Agricultural Experiment Station (OAES), "Smith's Gold," Certificate and Application for Plant Variety Protection, PVPO No. 201800136, filed Jan. 24, 2018, 15 pages.
Owens, K., Oklahoma Agricultural Experiment Station (OAES), "Strad CL Plus," Certificate and Application for Plant Variety Protection, PVPO No. 202100242, filed Mar. 17, 2021, 26 pages.
Watson, C., Oklahoma Agricultural Experiment Station (OAES), "Billings" Certificate and Application for Plant Variety Protection, PVPO No. 201000098, filed Jan. 21, 2010, 30 pages.

* cited by examiner

*Primary Examiner* — Cynthia E Collins
(74) *Attorney, Agent, or Firm* — McKee, Voorhees & Sease, PLC

(57) ABSTRACT

The disclosure relates to commercially elite hard red winter wheat varieties having increased dough strength. The wheat variety designated OK15MASBx7 ARS 8-29, the plants and seeds and plant parts of wheat variety OK15MASBx7 ARS 8-29, methods for producing a wheat plant produced by crossing the variety OK15MASBx7 ARS 8-29 with another wheat plant, and hybrid wheat seeds and plants produced by crossing the variety OK15MASBx7 ARS 8-29 with another wheat line or plant, and the creation of variants by mutagenesis or transformation of variety OK15MASBx7 ARS 8-29 are also provided. Methods for producing other wheat varieties or breeding lines derived from wheat variety OK15MASBx7 ARS 8-29 and wheat varieties or breeding lines produced by those methods are also provided. Further provided are commodity plant products from wheat varieties having increased dough strength.

29 Claims, 4 Drawing Sheets

WHEAT VARIETY OK15MASBx7 ARS 8-29

TECHNICAL FIELD

The present disclosure relates to the field of wheat breeding. In particular, this disclosure relates to a new wheat variety designated OK15MASBx7 ARS 8-29.

BACKGROUND

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, better agronomic quality, resistance to herbicides, and improvements in grain compositional traits. The reasons for this goal are to maximize the amount of grain produced on the land used and to supply food for both animals and humans. To accomplish this goal, the breeder must select and develop wheat plants that have traits that result in superior varieties.

Wheat may be classified into six different market classes. Five of these, including hard red winter, hard red spring, hard white, soft red winter, and soft white, belong to the species *Triticum aestivum* L., and the sixth, durum, belongs to the species *Triticum turgidum* conv. *durum*. Wheat may be used to produce a variety of products, including, but not limited to, grain, flour, baked goods, cereals, crackers, pasta, beverages, livestock feed, biofuel, straw, construction materials, and starches. The hard wheat classes are milled into flour used for breads, while the soft wheat classes are milled into flour used for pastries and crackers. Often, a wheat-based food will be produced from milled flour of two market classes, such as hard red winter and hard red spring, to achieve a certain blend of functionalities specifically suited for that wheat product. Additionally, food additives such as dough conditioners and vital wheat gluten, are included to further enhance the baking process and to compensate for deficiencies in the original milled flour itself. Wheat starch is used in the food and paper industries as laundry starches, among other products.

SUMMARY

The present disclosure relates to commercially elite hard red winter (HRW) wheat varieties having increased dough strength as compared to typical HRW wheat varieties. In some embodiments, the increased dough strength is due, in part, to overexpression of the wheat Bx7 subunit (Bx7oe). In some embodiments, dough strength is measured by mixing stability time and/or mixing tolerance index. The Bx7oe high-molecular weight glutenin subunit (HMW-GS) is encoded by the Glu-B1al allele and rarely occurs in hard winter wheat varieties despite HRW wheat being the primary market class grown in the United States. Wheat varieties having the Bx7oe subunit may possess increased dough strength, far exceeding ordinary HRW wheat varieties and in-line with the strongest hard red spring wheat varieties. More specifically, Bx7oe varieties may exhibit increased mixing tolerance.

In some embodiments, the variety comprising the Bx7oe subunit is wheat variety OK15MASBx7 ARS 8-29 or a wheat variety having OK15MASBx7 ARS 8-29 as an ancestor.

Methods of producing a commodity plant product are also provided. In some embodiments, the method comprises collecting the commodity plant product from an HRW wheat variety having increased dough strength. In some embodiments, the commodity plant product comprises at least once cell of wheat variety OK15MASBx7 ARS 8-29. The commodity plant product may be, but is not limited to oil, meal, grain, flour, vital wheat gluten flour, flour blends, baked goods, cereals, pasta, beverages, livestock feed, biofuel, straw, construction materials, or starches.

Plants of wheat variety OK15MASBx7 ARS 8-29 are also provided. Plants produced by growing the seed of wheat variety OK15MASBx7 ARS 8-29, as well as the derivatives of such plants are provided. Further provided are plant parts, including cells, plant protoplasts, plant cells of a tissue culture from which wheat plants may be regenerated, plant calli, plant clumps, and plant cells that are intact in plants or parts of plants, such as leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells, and the like.

Another embodiment relates to a tissue culture of regenerable cells of wheat variety OK15MASBx7 ARS 8-29, as well as plants regenerated therefrom, wherein the regenerated wheat plant is capable of expressing all of the morphological and physiological characteristics of a plant grown from the wheat seed designated OK15MASBx7 ARS 8-29.

Yet another embodiment is a wheat plant of the wheat variety OK15MASBx7 ARS 8-29 further comprising a locus conversion. In one embodiment, the wheat plant is defined as comprising the locus conversion and otherwise capable of expressing all of the morphological and physiological characteristics of the wheat variety OK15MASBx7 ARS 8-29. In particular embodiments of the disclosure, the locus conversion may comprise a transgene which has been introduced by genetic transformation into the wheat variety OK15MASBx7 ARS 8-29 or a progenitor thereof. In still other embodiments of the disclosure, the locus conversion may comprise a dominant or recessive allele. The locus conversion may confer potentially any trait upon the plant, including, but not limited to, herbicide resistance, insect resistance, resistance to bacterial, fungal, or viral disease, male fertility or sterility, and improved nutritional quality. One or more locus conversion traits may be introduced into a single wheat variety.

Still yet embodiment is a method of producing wheat seeds comprising crossing a plant of the wheat variety OK15MASBx7 ARS 8-29 to any second wheat plant, including itself, or another plant of the variety OK15MASBx7 ARS 8-29, or a plant that is not variety OK15MASBx7 ARS 8-29. In particular embodiments of the disclosure, the method of crossing comprises the steps of: (a) planting seeds of wheat variety OK15MASBx7 ARS 8-29; (b) cultivating wheat plants resulting from said seeds until said plants bear flowers; (c) allowing fertilization of the flowers of said plants; and (d) harvesting seeds produced from said plants.

Still yet another embodiment is a method for developing a wheat plant in a wheat breeding program comprising: (a) obtaining a wheat plant, or its parts, of the variety OK15MASBx7 ARS 8-29; and (b) employing said plant or parts as a source of breeding material using plant breeding techniques. In the method, the plant breeding techniques may be selected from the group consisting of recurrent selection, mass selection, bulk selection, backcrossing, pedigree breeding, genetic marker-assisted selection, gene editing and genetic transformation. In certain embodiments of the disclosure, the wheat plant of variety OK15MASBx7 ARS 8-29 may be used as the male or female parent.

The disclosure also provides methods of multiplication or propagation of wheat plants of the disclosure, which can be accomplished using any method known in the art, for example, via vegetative propagation and/or seed. The disclosure also encompasses the plantlets and plants produced by those methods.

In addition to the exemplary aspects and embodiments described above, further aspects and embodiments will become apparent by study of the following descriptions.

DETAILED DESCRIPTION

Figure 1:
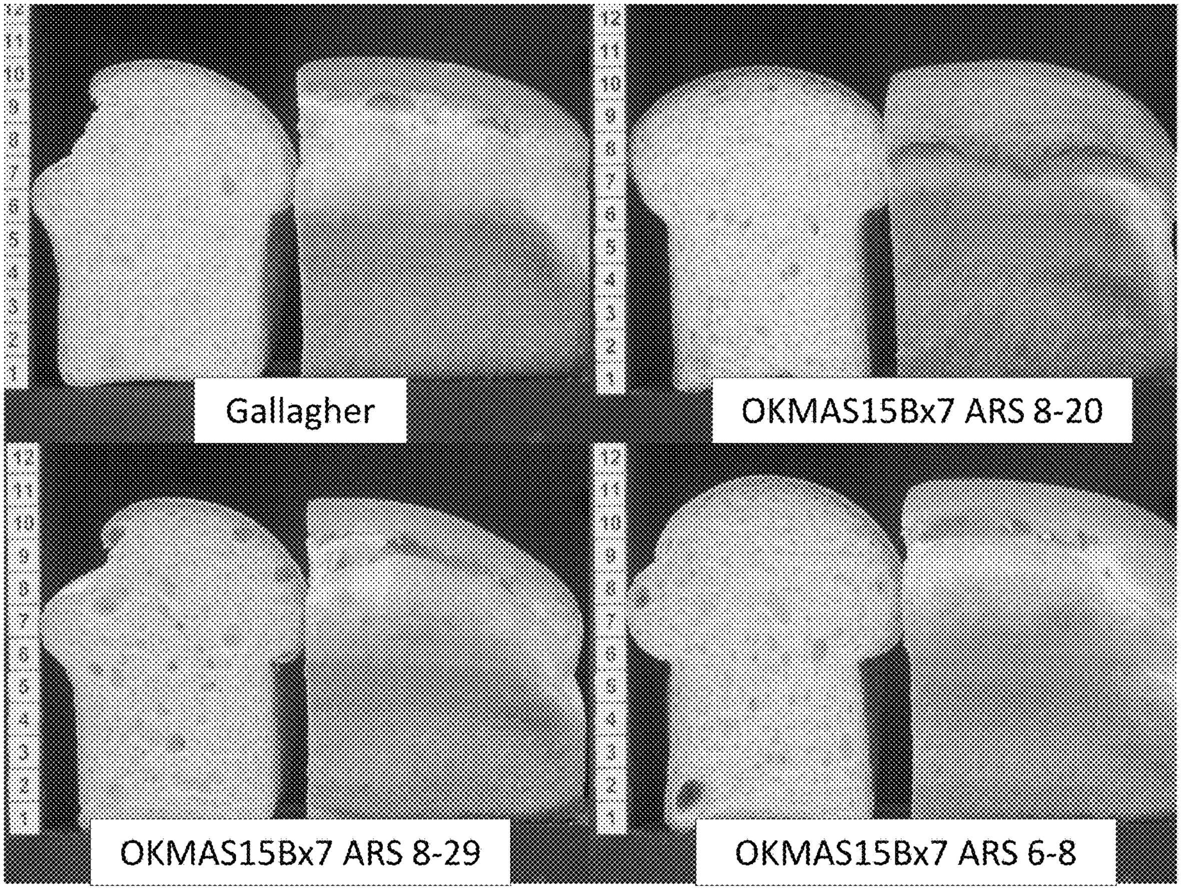
FIG. 1 compares bread baked from individual Hard Red Winter (HRW) non Bx7oe verses Bx7oe lines.

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Similarly, the word "or" is intended to include "and" unless the context clearly indicates otherwise. The word "or" means any one member of a particular list and also includes any combination of members of that list. Further, all units, prefixes, and symbols may be denoted in its SI accepted form.

An "allele" is any of one or more alternative forms of a genetic sequence. In a functionally diploid cell or organism, the two alleles of a given genetic sequence occupy corresponding loci on a pair of homologous chromosomes.

The term "backcrossing" refers to a process in which a breeder crosses progeny back to one of the parents one or more times, for example, a first generation hybrid $F_1$ with one of the parental genotypes of the $F_1$ hybrid.

A "cell" as used herein includes a plant cell, whether isolated, in tissue culture or incorporated in a plant or plant part. The cell can be a cell, such as a somatic cell, of the variety having the same set of chromosomes as the cells of the deposited seed, or, if the cell contains a locus conversion or transgene, otherwise having the same or essentially the same set of chromosomes as the cells of the deposited seed.

As used herein, the terms "commercially elite" and "commercially elite line" refer to any line that has resulted from breeding and selection for desirable agronomic performance (typically commercial production). Generally, individuals in a line have similar parentage and one or more similar traits. In some cases, a "commercially elite line" or "commercially elite variety" can be an agronomically superior line or variety that has resulted from many cycles of breeding and selection for superior agronomic performance. An "elite inbred line" is an elite line that is an inbred, and that has been shown to be useful for producing sufficiently high yielding and agronomically fit hybrid varieties (an "elite hybrid variety"). Similarly, "elite germplasm" is a germplasm resulting from breeding and selection for desirable agronomic performance (typically commercial production). Such germplasm may be agronomically superior germplasm, derived from and/or capable of giving rise to a plant with superior agronomic performance, such as an existing or newly developed elite line of wheat.

A "commodity plant product" refers to any composition or product that is comprised of material derived from a plant, seed, plant cell, or plant part of the present disclosure. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, fiber, flakes, bran, fiber, paper, tea, coffee, silage, crushed whole grain, and any other food for human or animal consumption; biomasses and fuel products; raw material in industry; and grain, flour, flour blends, baked goods, cereals, pasta, beverages, livestock feed, straw, construction material, and starches.

As used herein, "genome editing" or "gene editing" refers to a type of genetic engineering in which DNA is inserted, replaced, modified, or removed from a genome using artificially engineered nucleases. Examples include but are not limited to use of zinc finger nucleases (ZFNs), TAL effector nucleases (TALENs), meganucleases, CRISPR/Cas9, and other CRISPR related technologies.

As used herein, "increased dough strength" means a level of dough strength exceeding that of typical HRW wheat varieties. Increased dough strength is commonly associated with overexpression of the wheat Bx7 subunit (Bx7oe). In some embodiments, a wheat variety having increased dough strength will exhibit mixing stability times of more than 18 minutes, 19 minutes, 20 minutes, 25, minutes, 30 minutes, 40 minutes, 50 minutes, 60 minutes, 70 minutes, or any intervening range therein.

A "locus conversion" (also called a "trait conversion" or "gene conversion") refers to a plant or plants within a variety or line that have been modified in a manner that retains the overall genetics of the variety and further comprises one or more loci with a specific desired trait, such as but not limited to insect or pest control, disease control or herbicide tolerance. Examples of single locus conversions include mutant genes, transgenes and native traits finely mapped to a single locus. One or more locus conversion traits may be introduced into a single variety.

As used herein, the term "plant" includes plant cells, plant protoplasts, plant tissue, plant cells of tissue culture from which wheat plants can be regenerated, plant calli, plant clumps, and plant cells that are intact in plants, or parts of plants such as pollen, flowers, seeds, leaves, stems, and the like.

As used herein, "plant part" includes any part of a plant, such as a plant organ, a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a pod, a part of a pod, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, pericarp, a pistil, an anther, or a flower. Seed can be mature or immature. Pollen or ovules may be viable or non-viable. Also, any developmental stage is included, such as seedlings, cuttings prior or after rooting, mature plants or leaves.

As used herein, the term "progeny" refers to any plant resulting from a vegetative or sexual reproduction from one or more parent plants or descendants thereof. For instance, a progeny plant may be obtained by cloning or selfing of a parent plant or by crossing two parent plants and include selfings as well as the F1 or F2 or still further generations. An F1 is a first-generation progeny produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait), while an F2 may be (and usually is) a progeny resulting from self-pollination of said F1 hybrids.

A "single locus converted" plant refers to plants which are developed by a plant breeding technique called backcrossing or via genetic engineering wherein essentially all of the morphological and physiological characteristics of a variety are recovered in addition to the desired trait or characteristics conferred by the single locus transferred into the variety via the backcrossing technique or via genetic engineering. A single locus may comprise one gene, or in the case of transgenic plants, one or more transgenes integrated into the host genome at a single site (locus).

A "transgene" refers to a nucleic acid of interest that can be introduced into the genome of a plant by genetic engineering techniques (e.g., transformation).

Bx7oe Line Development

Disclosed herein are commercially elite hard red winter (HRW) wheat varieties having increased dough strength as compared to typical HRW wheat varieties. In some embodiments, the increased dough strength is due, in part, to overexpression of the wheat Bx7 subunit (Bx7oe). The Bx7oe high-molecular weight glutenin subunit (HMW-GS) is encoded by the Glu-B1al allele. The overexpression of the wheat Bx7 subunit is associated with increased gluten strength. Success was already demonstrated in producing Glu-B1al-elevated dough strength in hard white cultivars, but reluctance has prevailed in distributing Glu-B1al beyond hard white wheat into the predominant market class of the U.S. Great Plains, HRW wheat. With the growing reliance on high-speed baking operations, there has been increased demand for HRW flour with sufficient dough strength. Simultaneously, HRW variety development has focused on high yield, rather than dough strength. Accordingly, a breeding program was developed to build upon the dough strength already present in some hard white wheat varieties and distribute it more widely to HRW wheat with a known and selectable breeding target, the Bx7oe subunit.

A recurrent, multi-trait, marker-assisted, backcross breeding strategy was initiated in 2012 to introduce targeted genes believed to represent a step-change improvement in disease resistance and functionality of wheat germplasm. The purpose was not to introgress all gene targets into the same background, but to strategically inject them each into distinct lineages within the wheat breeding program, and subsequently intercross between lineages to achieve the desired breadth and depth of introgression.

To accomplish this objective, four diverse backgrounds were chosen as recipients for introgression. Using available molecular markers at the time, a simple backcrossing procedure was used in Manhattan, Kansas to carry forward the Glu-B1al allele in the heterozygous condition through the $BC_2F_1$ generation. Two $BC_2F_1$ plants were selected per background to produce $BC_2F_2$ plants (conventional track) and $BC_2D_0$ plants (doubled haploid track). Only those homozygous for Glu-B1al were retained for subsequent increase in either track. In 2016, the $BC_2F_{2:3}$ (n=89) and $BC_2D_2$ (n=50) lines were increased in a greenhouse in Stillwater, Oklahoma to enable field testing in 2017.

Of the 139 $BC_2F_{2:3}$ and $BC_2D_2$ lines increased in 2016, 124 lines produced sufficient seed for field selection. The 2017 field nursery was established as a non-replicated, two-location trial at Lahoma and Goodwell, Oklahoma with check plots containing the original recipient parents. Selection was based on maturity pattern, reactions to leaf rust and stripe rust, straw strength, grain yield, volumetric grain weight, mixing tolerance derived from visual rating of a mixogram, and a dough strength index derived from mixograph band width at two minutes past peak dough development, mixograph stability, and SDS-sedimentation volume. Wide differences occurred among lines for dough strength, even though all lines descended from single plants homozygous for the Glu-B1al allele. Thus breeding for uniformity in dough strength is much more complicated that simply selecting for Bx7oe, as Bx7oe alone does not guarantee increased dough strength. Forty-one experimental lines ($BC_2F_{2:5}$ and $BC_2D_4$) were selected for extensive statewide replicated yield and quality trials beginning with the 2017-18 season. OK15MASBx7 ARS 8-29 was one of these selections.

Wheat Variety OK15MASBx7 ARS 8-29

In an embodiment, the disclosure is directed to *Triticum aestivum* variety OK15MASBx7 ARS 8-29, its seeds, plants, and hybrids. Wheat variety OK15MASBx7 ARS 8-29 based on grain morphology would be classified as a hard red winter (HRW) type common wheat bred for the winter wheat growing regions of the United States. The primary usage of wheat variety OK15MASBx7 ARS 8-29 will be for production of grain, with particular potential as a blending wheat to increase the strength of the average HRW blend intended for use in products requiring more gluten strength, such as pan breads, noodles, and frozen dough. Other potential uses include, but are not limited to, production of silage harvested in the soft dough stage, hay, or grazed for feed.

Wheat variety OK15MASBx7 ARS 8-29 is a conventionally inbred progeny originating from a backcross made in Stillwater, Oklahoma between a commercially available HRW wheat variety and a proprietary hard white winter wheat variety comprising the Bx7 overexpression subunit (Bx7oe). The central rationale for this backcross was to introgress the Bx7oe subunit from the hard white winter variety into an elite HRW background, while at the same time selecting against less desirable characteristics of the HRW parent, to result in a new HRW variety with high yield potential and excellent end-use quality.

OK15MASBx7 ARS 8-29 has shown no significant variants other than what would normally be expected due to the environment.

In accordance with an aspect of the disclosure, there is provided a wheat plant having the morphological and physiological characteristics of OK15MASBx7 ARS 8-29 as presented in Table 1 and Table 2, below. Those of skill in the art will recognize that these are typical values that may vary due to environment and that other values that are substantially equivalent are within the scope of the disclosure.

TABLE 1

Phenotypic Description of Wheat (*Triticum aestivum*) Variety OK15MASBx7 ARS 8-20

| | |
|---|---|
| **Plant** | |
| Plant Kind | Common |
| Market Class | HRW (Hard Red Winter) |
| Vernalization | Winter |
| Coleoptile Anthocyanin | Absent |
| Juvenile Plant Growth | Semi-Erect |
| Plant Color (Boot Stage) | Green |
| Flag Leaf Orientation (Boot Stage) | Erect to Semi-Erect |
| Flag Leaf Type | Twisted |
| Flag Leaf Glaucosity | Wax Present |
| **Ear** | |
| Ear Emergence (No. of Days) | 91; 1 day earlier than 'Doublestop CL Plus', same number of days as 'Smith's Gold', 2 days later than 'Gallagher' |
| **Anther** | |
| Anther Coloration | Yellow |
| **Plant Height** | |
| Plant Height Class | Semi-Dwarf |
| Plant Height (cm) | 89; 1 cm taller than 'Breakthrough', same height as 'Uncharted', 9 cm shorter than 'Showdown' |
| **Stem** | |
| Stem Anthocyanin Coloration | Absent |
| Stem Waxy Bloom | Present |
| Stem Hairiness (Last Internode of Rachis) | Present |
| Internode Type | Hollow |
| Number of Nodes | 4 |
| Peduncle Type | Erect |
| Peduncle Length (cm) | 23 |
| Auricle Anthocyanin | Absent |
| Auricle Hairiness | Absent |
| **Head** | |
| Head Density at Maturity | Lax |
| Head Shape at Maturity | Strap |
| Head Curvature at Maturity | Recurved |
| Head Awnedness at Maturity | Awned |
| **Glume** | |
| Glume Color at Maturity | White |
| Glume Shoulder at Maturity | Oblique |
| Glume Shoulder Width at Maturity | Narrow to Medium |
| Glume Beak Shape at Maturity | Acuminate |
| Glume Beak Length at Maturity | Medium; 5 mm |
| Glume Beak Width at Maturity | Narrow; 1 mm |
| Glume Length at Maturity | Medium; ~8 mm |
| Glume Width at Maturity | Wide; ~4 mm |
| Glume Pubescence at Maturity | Absent |
| **Seed** | |
| Seed Shape | Ovate to Elliptical |
| Seed Cheek | Rounded |
| Seed Brush | Short to Medium |
| Seed Brush Collar | Not Collared |
| Seed Crease Width | Narrow (Width of 60% or less of kernel) |
| Seed Crease Depth | Mid-deep (Depth of 25% or less of kernel) |
| Seed Color | Red |
| Seed Texture | Hard |
| Seed Weight (g/1000 seeds) | 35 |

TABLE 1-continued

| Phenotypic Description of Wheat (*Triticum aestivum*) Variety OK15MASBx7 ARS 8-20 | |
|---|---|
| Seed Germ Size | Medium |
| Disease | |
| Stem Rust (*Puccinia graminis* 6. sp. *tritici*) | Intermediate; US Races |
| Leaf Rust (*Puccinia recondita* 6. sp. *tritici*) | Resistant; Field Reaction |
| Stripe Rust (*Puccinia striiformis*) | Resistant; Field Reaction |
| Powdery Mildew (*Erysiphe graminis* 6. sp. *tritici*) | Resistant; Field Reaction |
| Tan Spot (*Pyrenophora tritici-repentis*) | Susceptible; Oklahoma Isolates |
| *Septoria tritici* (Speckled Leaf Blotch) | Susceptible; Field Reaction |
| Barley Yellow Dwarf Virus (BYDV) | Tolerant; Field Reaction |
| Soilborne Mosaic Virus (SBMV) | Intermediate; Field Reaction |
| Wheat Yellow (Spindle Streak) Mosaic Virus | Intermediate; Field Reaction |
| Wheat Streak Mosaic Virus (WSMV) | Susceptible; Field Reaction |
| Pests | |
| Hessian Fly (*Mayetiola destructor*) Biotype GP | Resistant |
| High Molecular Weight Glutenin Subunit Profile | |
| Glu-A1 | 2* |
| Glu-B1 | Bx7oe + 8 |
| Glu-D1 | 5 + 10 |
| Translocations | |
| 1BL/1RS | Absent |
| 1A/1R | Absent |
| 2NS/2AS | Absent |
| 4DL/4AgS | Absent |
| Herbicide Tolerance | |
| Imadazoline Tolerance Genes | Absent |
| Quizalofop Tolerance Genes | Absent |
| End Use Quality | |
| Farinograph | 40-80 Minutes in stability time |

TABLE 2

Molecular marker assays for comparative HRW variety 'Gallagher' and Bx7oe varieties OK15DMASBx7 ARS 6-8, OK15MASBx7 ARS 8-20, and OK15MASBx7 ARS 8-29. The two full sib lines, OK15MASBx7 ARS 8-20 and OK15MASBx7 ARS 8-29, may be distinguished from OK15DMASBx7 ARS 6-8 by differences at the Lr34, Lr68, and Lr77 marker loci. The two sib lines may be distinguished from each other at the Sbm1 marker locus and from 'Gallagher' by the presence of T1RS.BL in 'Gallagher' and expected difference at the Glu-B1 locus. Target gene presence is considered doubtful when indicated by "?".

| | Gallagher | OK15MASBx7 ARS 8-20 | OK15MASBx7 ARS 8-29 | OK15DMASBx7 ARS 6-8 |
|---|---|---|---|---|
| Leaf Rust | | | | |
| Lr21 | – | – | – | – |
| Lr24/Sr24 | – | – | – | – |
| Lr34/Yr18/Bdv1 | – | – | – | + |
| Lr37/Sr38/Yr17 | – | – | – | + |
| Lr42 | – | – | – | – |
| Lr46 | – | – | – | – |
| Lr67 | – | – | – | – |
| Lr68 | + | + | + | – |
| Lr77 | + | + | + | – |
| Stripe Rust | | | | |
| Yr5 | ? | ? | ? | ? |
| Yr15 | – | – | – | – |
| Yr36 | – | – | – | – |
| Stem Rust | | | | |
| Sr2 | – | – | – | – |
| Sr22 | – | – | – | – |
| Sr26 | – | – | – | – |
| Sr35 | – | – | – | – |
| Sr36/Pm6 | – | – | – | – |
| SrTmp | – | – | – | – |

TABLE 2-continued

Molecular marker assays for comparative HRW variety 'Gallagher' and Bx7oe varieties OK15DMASBx7 ARS 6-8, OK15MASBx7 ARS 8-20, and OK15MASBx7 ARS 8-29. The two full sib lines, OK15MASBx7 ARS 8-20 and OK15MASBx7 ARS 8-29, may be distinguished from OK15DMASBx7 ARS 6-8 by differences at the Lr34, Lr68, and Lr77 marker loci. The two sib lines may be distinguished from each other at the Sbm1 marker locus and from 'Gallagher' by the presence of T1RS.BL in 'Gallagher' and expected difference at the Glu-B1 locus. Target gene presence is considered doubtful when indicated by "?".

| | Gallagher | OK15MASBx7 ARS 8-20 | OK15MASBx7 ARS 8-29 | OK15DMASBx7 ARS 6-8 |
|---|---|---|---|---|
| | | Viruses | | |
| Bdv2 | − | − | − | − |
| Sbm1 | + | + | − | + |
| | | HMW-GS | | |
| Glu-A1 | 2* | 2* | 2* | 2* |
| Glu-B1 | 7 + 9 | $7^{oe}$ + 8 | $7^{oe}$ + 8 | $7^{oe}$ + 8 |
| Glu-D1 | 5 + 10 | 5 + 10 | 5 + 10 | 5 + 10 |
| 1RS | + | − | − | − |
| Translocation | TIRS.1BL | None | None | None |

Dough Strength

The presence of the Glu-B1al allele, and potential interaction with other yet unidentified alleles at loci that additionally influence dough strength, can impart a level of dough strength in HRW wheat that parallels that of the strongest hard red spring (HRS) varieties and far exceeds existing ordinary HRW wheat varieties.

The industry standard for measuring dough strength for many food applications is a recording dough mixer called the farinograph. Dough strength is a preferred attribute especially for bread baking, and less so for confectionary products. A weaker dough is universally signified by a shorter stability time, which is often associated with shorter peak dough development time. The mixing tolerance index (MTI) measures the decline in the recording curve, or degree of breakdown in dough strength, at five minutes past the peak time. This may reflect dough strength, as greater MTI values signify a weaker dough. Water absorption reflects the amount of water required for optimal dough mixing. This parameter may be unrelated to the strength indicators above at a given kernel hardness level, but for bread baking applications, higher water absorption values are preferred.

The farinograph is highly subject to operator error, which may prevent proper hydration of doughs that vary widely in water uptake pattern. The stability time may be further under-estimated for excessively strong genotypes as a quirk of the farinograph software, which should calculate stability time as the difference in arrival time, or first hydration peak, and the departure time. In other cases, operators have been known to prematurely terminate a farinograph run of the candidate lines by inaccurately identifying the true peak development time. This may explain, in part, the wide range of values generated among cooperators shown in Table 3. Results were reported as they were received, with this known caveat.

Uniquely elevated dough strength of OK15MASBx7 ARS 8-29 and two other candidates (OK15DMASBx7 ARS 6-8 and OK15MASBx7 ARS 8-20) was manifested in unusually long farinograph stability and peak dough development times, as shown below in Table 3. Thus, all candidates possessed a level of dough strength, based upon those two key parameters, far exceeding ordinary HRW wheat cultivars. The dough strength of OK15MASBx7 ARS 8-20 and OK15MASBx7 ARS 8-29 is considered parallel to that of the strongest hard red spring wheat cultivars common in the northern U.S. and in Canada. The dough strength of OK15DMASBx7 ARS 6-8 is less overbearing and more balanced with dough extensibility, though still stronger than ordinary HRW wheat. Flour water absorption tended to be elevated in the candidates relative to ordinary HRW wheat, but not at a level that could be declared statistically significant in this set of flour samples. Likewise, the MTI tended to be lower (higher dough strength), but variability in the results produced an observed significance level of about 10%. It is preferred to account for the entire mixing curve rather than a five-minute segment that might be more appropriate for doughs with much shorter and more typical stability times of five to ten minutes.

TABLE 3

Common farinograph parameters provided by seven industry collaborators for seven wheat samples produced in Oklahoma during the period 2019 to 2021. The HRW control genotype was 'Gallagher' (Tests 1-3, 7), 'Jagalene' (Tests 4, 5), and an experimental with HRW functionality (Test 6).

| Test | Crop year | OK15MASBx7 ARS 20-Aug | OK15MASBx7 ARS 29-Aug | OK15DMASBx7 ARS 6-8 | HRW control | OK15MASBx7 ARS 20-Aug | OK15MASBx7 ARS 29-Aug | OK15DMASBx7 ARS 6-8 | HRW control |
|---|---|---|---|---|---|---|---|---|---|
| | | Stability, min | | | | Peak time, min | | | |
| 1 | 2019 | 19.1 | 19.3 | 18.9 | 16 | 8.1 | 7.2 | 4.8 | 3.9 |
| 2 | 2020 | 18.9 | 17.8 | 18.5 | 13.7 | 8 | 5.7 | 6.2 | 7.1 |
| 3 | 2020 | 74.3 | 77.1 | 59.4 | 16.1 | 58.6 | 63 | 44.5 | 2.7 |
| 4 | 2020 | 48 | | | 12.1 | 30.2 | | | 6.9 |
| 5 | 2021 | | 54.5 | 26.5 | 12.7 | | 40.6 | 9.3 | 6 |

TABLE 3-continued

Common farinograph parameters provided by seven industry collaborators for seven wheat samples produced in Oklahoma during the period 2019 to 2021. The HRW control genotype was 'Gallagher' (Tests 1-3, 7), 'Jagalene' (Tests 4, 5), and an experimental with HRW functionality (Test 6).

| Test | Crop year | OK15MASBx7 ARS 20-Aug | OK15MASBx7 ARS 29-Aug | OK15DMASBx7 ARS 6-8 | HRW control | OK15MASBx7 ARS 20-Aug | OK15MASBx7 ARS 29-Aug | OK15DMASBx7 ARS 6-8 | HRW control |
|---|---|---|---|---|---|---|---|---|---|
| 6 | 2021 | 42.8 | 46.1 | 25 | 9.3 | 30.1 | 28.6 | 12.4 | 6 |
| 7 | 2021 | | 43.7 | 30 | 11.8 | | 34.7 | 10.5 | 6.6 |
| | Mean | 40.6 | 43.1 | 29.7 | 13.1 | 27 | 30 | 14.6 | 5.6 |
| | t test vs HRW control (P value) | 0.005 | 0.002 | 0.008 | | 0.01 | 0.006 | 0.069 | |
| | | Absorption, % | | | | MTI | | | |
| 1 | 2019 | 58.7 | 59.5 | 58.4 | 57.2 | 17 | 15 | 19 | 5 |
| 2 | 2020 | 63.1 | 63.2 | 62.3 | 61.8 | 3 | 20 | 5 | 24 |
| 3 | 2020 | 63.1 | 64.2 | 61.4 | 61.2 | 3 | 6 | 8 | 9 |
| 4 | 2020 | 62.1 | | | 57.1 | 10 | | | 22 |
| 5 | 2021 | | 70.2 | 68.7 | 67.7 | | 0 | 17 | 14 |
| 6 | 2021 | 64 | 61.9 | 62.2 | 58.9 | 15 | 10 | 17 | 37 |
| 7 | 2021 | | 61.4 | 57.9 | 58.8 | | 18 | 9 | 21 |
| | Mean | 62.2 | 63.4 | 61.8 | 60.4 | 9.6 | 11.5 | 12.5 | 18.9 |
| | t test vs HRW control (P value) | 0.227 | 0.112 | 0.214 | | 0.082 | 0.104 | 0.194 | |

Figure 2:
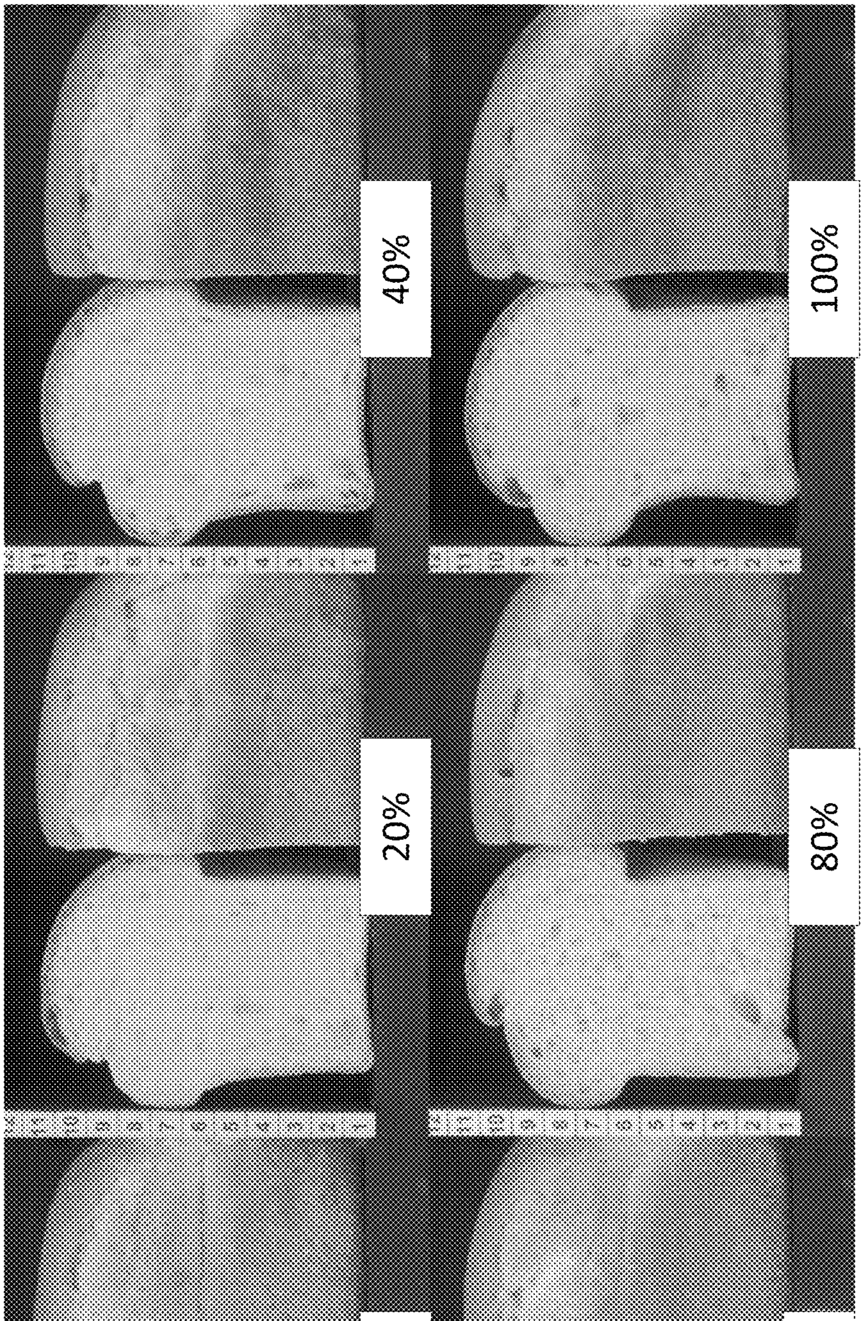
FIG. 2 compares bread baked from Bx7oe wheat blends, percentage of Bx7oe ranging from 0% to 100%.

Wheat variety OK15DMASBx7 ARS 8-29 was further evaluated along with two other HRW Bx7 over expression (Bx7oe) lines (OK15DMASBx7 ARS 6-8 and OK15MASBx7 ARS 8-20) and an HRW control ('Gallagher'; PV 201300134) for suitability as HRW blending wheats for increased strength. The results are presented in FIGS. 1 and 2.

Milling Results

'Gallagher' yielded the greatest flour extraction at 78.9%. The data show lower percentages of bran, indicating cleaner separation of the endosperm from the bran and/or a thinner bran coating. OK15DMASBx7 ARS 6-8 yielded the best flour extraction of the Bx7oe lines at 77.0%, likely due to a thinner bran fraction compared to the other experimental lines. OK15MASBx7 ARS 8-20 and 8-29 had similar flour extractions of 73.3% and 73.1%, respectively, values within the range for HRW flour extraction.

Flour Quality Results

HRW varieties comprising the Bx7oe subunit exhibit superior mixing stability and better resistance to over-mixing as compared to ordinary HRW varieties.

In farinograph testing, water absorption (WA) values were acceptable for all Bx7oe HRW lines. Indeed, the WA were all on the high end for HRW. This is a notable achievement given the average WA of ~58-60% for most HRW varieties available in the market. Comparative variety 'Gallagher' had a WA value of 61.2%, which is considered a very good WA value for HRW. OK15MASBx7 ARS 8-20 and 8-29 were even better than 'Gallagher' and had WA values of 63.1% and 64.2%, respectively. These are considered exceptional WA values for HRW and consistent with WA values for high quality hard red spring varieties.

'Gallagher' presented with good HRW peak time (2.7 min), mixing stability (16 min), and mixing tolerance index (MTI) values (9 BU). The stability and MTI values in particular show 'Gallagher' to be a higher quality HRW than average. Mixing stabilities of over 10 min indicate good resistance to over-mixing and are considered strong for HRW. An MTI of less than 10 BU indicates little to no breakdown in the first 5 minutes after peak. MTI values of ≤10 BU are more common to strong hard red spring (HRS) varieties.

All Bx7oe lines tested required in excess of 40 minutes to achieve a mixing peak. This level of stability is not common in U.S. HRW or HRS wheat classes. It is most commonly observed in varieties classified as Canadian Western Extra Strong (CWES), as an example. OK15DMASBx7 ARS 6-8 presented with the shortest peak time (44.5 min) of all the Bx7oe lines. Mixing stability was just under an hour (59.4 min) with an MTI of 8 BU. OK15MASBx7 ARS 8-20 and 8-29 presented with peak times of 58.6 min and 63.0 min, mixing stabilities of 74.3 min and 77.1 min, and MTI values of 3 BU and 6 BU, respectively. Both OK15MASBx7 ARS 8-20 and 8-29 are significantly stronger than OKDMASBx7 ARS 6-8 and would be considered to be statistically similar, but for stability time, to one another.

Alveograph: Alveograph P (104 mm), L (107 mm), and P/L values (0.97) for 'Gallagher' are typical for a high quality HRW with balanced strength and extensibility characteristics. OK15DMASBx7 ARS 6-8 showed a similar Alveograph profile with P=109, L=117, and P/L=0.93. Both of these samples required only the standard 8 min Alveograph mixing protocol. OK15MASBx7 ARS 8-20 and 8-29 required adjustment of the protocol to accommodate 18 min of mixing to achieve full development of the sample. Correspondingly, both samples showed strong Alveograph characteristics. OK15MASBx7 ARS 8-20 had values of P=195 mm, L=47 mm, and P/L=4.15, whereas OK15MASBx7 ARS 8-29 had values of P=203 mm, L=29 mm, and P/L=7.00. While both should be considered statistically similar to one another, the pattern suggested by the Farinograph and Alveograph results indicate that OK15MASBx7 ARS 8-29 tends to be stronger than 8-20, and this may approach significance in certain growing years and/or locations.

Bread Baking Results

HRW varieties comprising the Bx7oe subunit also exhibit superior bread baking qualities as compared to typical HRW varieties and show particular potential for use as strengthening components of bread flour blends.

To evaluate bread baking qualities, water was added in two stages (1st stage addition of ~75%; 2nd stage gradual addition of the remainder) during dough mixing to prevent any smearing in the bowl. This issue is sometimes encountered using the traditional pup loaf pin mixer set-up common in most bread quality labs. Making this adjustment ensured proper hydration and water uptake during mixing so that baking performance was not compromised. This adjustment would not be necessary in a commercial bakery if the Bx7oe lines were incorporated at low levels as strengthening components of a bread flour blend.

Baking notes indicated that OK15MASBx7 ARS 8-29 presented some difficulties during dough mixing with a slightly bucky feel to the final dough, likely due to its slightly greater strength compared to the other Bx7oe lines. However, it is likely that blending would mitigate these issues, especially if blends are kept on the lower end of the range (i.e., below 40% of the total flour blend). OK15MASBx7 ARS 8-20 and OK15DMASBx7 ARS 6-8 did not present with mixing challenges or dough handling issues and would likely move smoothly into bakery production as strengthening components in a bread flour blend.

The control HRW, 'Gallagher', showed good HRW baking quality with an average loaf volume of 812 cc and an average specific volume of 5.83 cc/g. OK15MASBx7 ARS 8-20 and 8-29 were not far behind 'Gallagher' with average loaf volumes of 802 cc and 782 cc and specific loaf volumes of 5.79 cc/g and 5.63 cc/g, respectively. OK15MASBx7 ARS 8-20 had a slightly better average internal crumb score (6.9) than OK15MASBx7 ARS 8-29 (6.0) or 'Gallagher' (6.75). OK15DMASBx7 ARS 6-8 showed the greatest average loaf volume and specific loaf volume of all the treatments, coming in at 942 cc and 6.86 cc/g, respectively.

Bx7oe Flour Blends

Typical flour comprises a blend of multiple wheat varieties. To evaluate potential use of Bx7oe HRW varieties as part of flour blends, 6 blends of varying Bx7oe percentages were evaluated (0% Bx7oe, 20% Bx7oe, 40% Bx7oe, 60% Bx7oe, 80% Bx7oe, and 100% Bx7oe). Candidate OK15MASBx7 ARS 8-29 was used as the representative Bx7oe HRW blending wheat with the HRW variety 'Big Max' as the common flour source.

Milling Results

Flour extraction ranged from 71.1% (40% Bx7oe) to 73.7% (60% Bx7oe) across the blends with lower extractions observed below 40% Bx7oe. This indicates that the presence of a Bx7oe in a wheat blend does not necessarily result in lower extraction.

Flour Quality Results

Figure 3A:
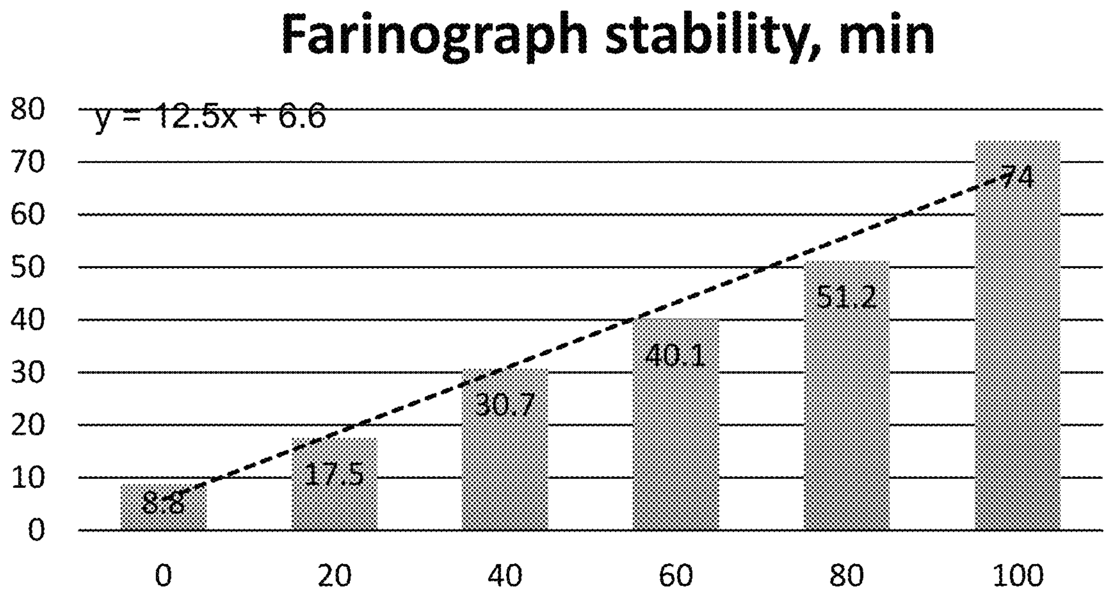
FIG. 3A-D depicts farinograph parameters in response to increasing inclusion rate of OK15MAS Bx7 ARS 8-29 flour with 'Big Max' flour (common HRW cultivar). Inclusion rates of 0 and 100% respectively represent pure flour samples of Big Max and OK15MAS Bx7 ARS. 3A depicts farinograph stability, 3B depicts farinograph peak time, 3C depicts farinograph absorption, and 3D depicts farinograph mixing tolerance index (MTI).
Figure 3B:
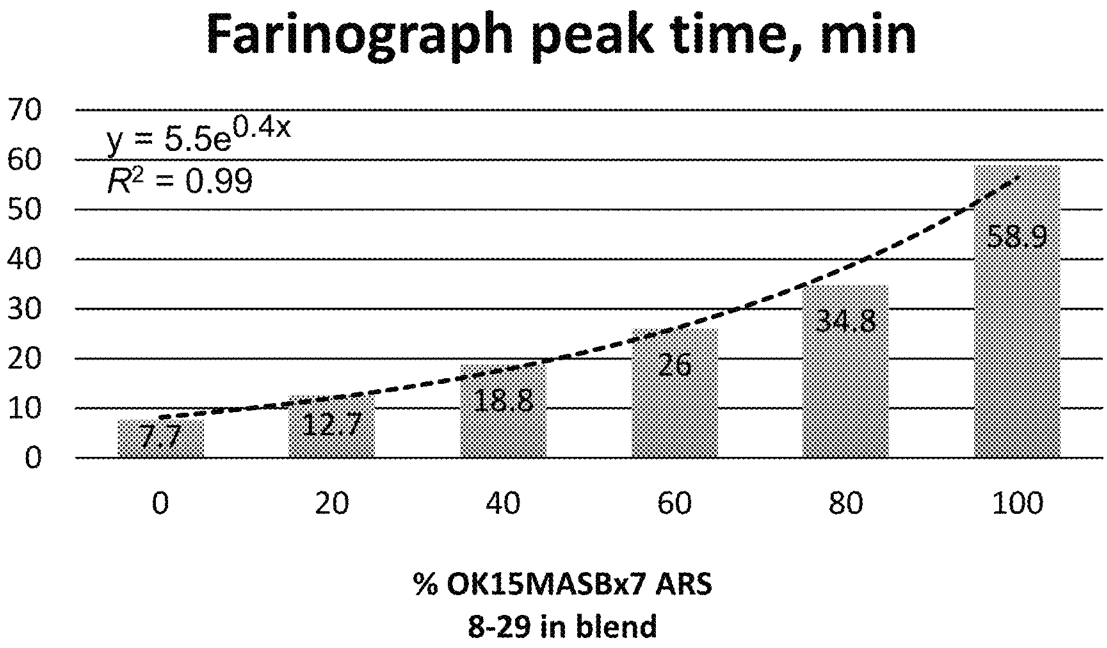
Figure 3C:
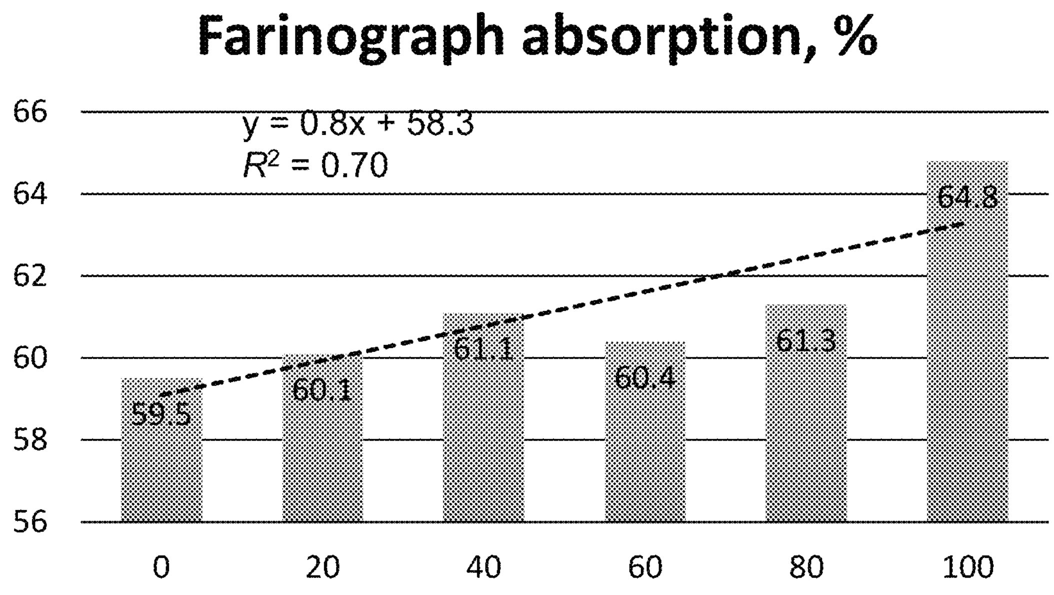
Figure 3D:
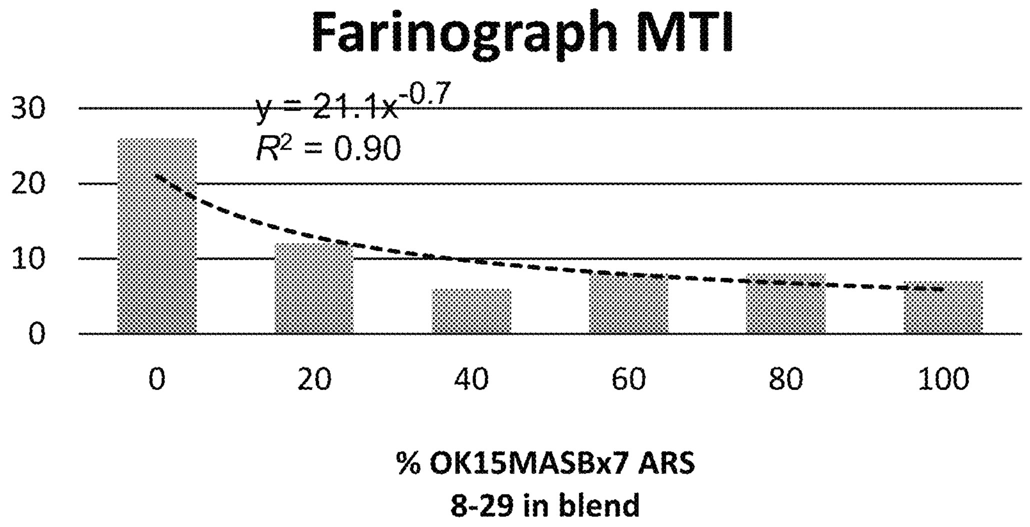

Farinograph—WA, peak time, and mixing stability steadily increased with increasing percentages of Bx7oe in the blend, as expected. WA of the 0% Bx7oe was 59.5% compared to 64.8% for the 100% Bx7oe (FIG. 3C). Peak time (FIG. 3B) and mixing stability (FIG. 3A) increased from 7.7 min and 8.8 min, respectively, to 58.9 min and ~74.0 min over the same 0-100% Bx7oe range. Ideal Farinograph characteristics were observed in the 20-40% Bx7oe range (60.1-61.1% WA; 12.7-18.8 min peak time; 17.5-30.7 min stability).

Alveograph—Alveograph trends were similar to those observed for the Farinograph. Strength increased and extensibility decreased as the blends progressed from 0-100% Bx7oe. P, L, and P/L values for 0% Bx7oe were 54 mm, 150 mm, and 0.36, respectively. These values were P=210 mm, L=35 mm, and P/L=6.0 for 100% Bx7oe. Starting with the 60% Bx7oe sample, the Alveograph mixing time was increased from the standard 8 min to 12 min (60% and 80% Bx7oe) or 18 min (100% Bx7oe) to allow for more optimal dough development in these stronger blends. Ideal Alveograph characteristics were observed in the 40-60% Bx7oe range (108-113 mm P; 108-97 mm L; 1.00-1.16 P/L).

Bread Baking Quality

Water was added in two stages (1st stage addition of ~75%; 2nd stage gradual addition of the remainder) during dough mixing starting with 60% Bx7oe to prevent any smearing in the bowl. This issue is sometimes encountered using the traditional pup loaf pin mixer set-up common in most bread quality labs. Making this adjustment ensured proper hydration and water uptake during mixing so that baking performance was not compromised. This adjustment was not necessary below 60% Bx7oe.

Baking notes indicated that 100% Bx7oe presented some difficulties during dough mixing with a slightly bucky feel to the final dough, likely due to its slightly greater strength compared to the other blends. The dough handling characteristics were best for 60% Bx7oe with doughs below this percentage being noted as slack. Doughs for 80% and 100% Bx7oe were noted as slightly bucky.

Average loaf volume and specific loaf volume were slightly better at 60% Bx7oe (876 cc and 6.28 cc/g, respectively) relative to other blends, but this difference is not statistically significant. Loaf volumes ranged from 838-888 cc with associated specific volumes of 5.99-6.37 cc/g, respectively. This range is comparatively small relative to the blending scale, and it indicates that the non-Bx7oe component of the blend controls most of the loaf volume response. The best average internal crumb score (6.9) was recorded for 40% Bx7oe, with all other blends containing any amount of Bx7oe average out at 6.5. The 0% Bx7oe average internal crumb score was 6.4.

Overall, the incorporation of Bx7oe as the strengthening component of a bread flour blend yielded improvements in its dough strength and handling properties, thereby retaining quality features while improving the baking process. The improvement in water absorption, mixing, and dough handling characteristics would be highly desirable from a commercial bakery standpoint.

Overall, testing results indicate wheat variety OK15MASBx7 ARS 8-29 is significantly stronger than the average HRW variety. OK15MASBx7 ARS 8-29 has strong dough characteristics, exceptional water absorption values, and high internal crumb score. OK15MASBx7 ARS 8-29 has potential for use as a blending wheat to increase the strength of the average HRW blend intended for use in products requiring more gluten strength, such as pan breads, noodles, and frozen dough.

TABLE 4

Full trial data from HRW Bx7oe Line Evaluation and Blending common HRW flour with Bx7oe flour.

| | 0 Bx7oe | 20 Bx7oe | 40 Bx7oe | 60 Bx7oe | 80 Bx7oe | 100 Bx7oe | Typical HRW wheat variety, such as Gallagher | OK15MASBx7 ARS 8-20 | OK15MASBx7 ARS 8-29 | OK15DMASBx7 ARS 6-8 |
|---|---|---|---|---|---|---|---|---|---|---|
| Whole Kernel Moisture %) | 12.6 | 12.5 | 12.3 | 12.3 | 12.2 | 12.1 | 11.8 | 11.4 | 11.8 | 11.3 |
| Buhler Test Mill Data | | | | | | | | | | |
| Bran (%) | 22.3 | 22.3 | 22.7 | 20.3 | 20.3 | 19.5 | 13.8 | 19.8 | 19.7 | 15.9 |
| Shorts (%) | 5.6 | 6.1 | 6.2 | 6.0 | 6.3 | 6.9 | 7.4 | 6.9 | 7.2 | 7.1 |
| Flour Extraction (%) | 72.2 | 71.6 | 71.1 | 73.7 | 73.4 | 73.6 | 78.9 | 73.3 | 73.1 | 77.0 |
| Moisture (%) | 14.2 | 13.9 | 14.1 | 13.6 | 13.5 | 13.9 | 13.8 | 13.4 | 13.2 | 13.6 |
| Farinograph Data (300 g bowl) | | | | | | | | | | |
| Absorption (14% mb) | 59.5 | 60.1 | 61.1 | 60.4 | 61.3 | 64.8 | 61.2 | 63.1 | 64.2 | 61.4 |
| Peak Time (min) | 7.7 | 12.7 | 18.8 | 26.0 | 34.8 | 58.9 | 2.7 | 58.6 | 63.0 | 44.5 |
| Stability Time (min) | 8.8 | 17.5 | 30.7 | 40.1 | 51.2 | 34.3 / 74.0 | 16.1 | 74.3 | 77.1 | 59.4 |
| Mixing Tolerance Index (BU) | 26 | 12 | 6 | 8 | 8 | 7 | 9 | 3 | 6 | 8 |
| Alveograph Data (Constant Hydration) | | | | | | | | | | |
| Maximum Overpressure, P (mm H2O) | 54 | 82 | 108 | 113 | 142 | 210 | 104 | 195 | 203 | 109 |
| Abscissa to Rupture, L (mm) | 150 | 137 | 108 | 97 | 62 | 35 | 107 | 47 | 29 | 117 |
| Swelling Index, G | 27.2 | 26.0 | 23.1 | 21.9 | 17.5 | 13.1 | 23.0 | 15.2 | 12.0 | 24.0 |
| Deformation Energy, W ($\times 10^{-4}$ J) | 237 | 351 | 426 | 410 | 376 | 342 | 369 | 411 | 267 | 515 |
| P/L | 0.36 8 min mixing | 0.60 8 min mixing | 1.00 8 min mixing | 1.16 12 min mixing | 2.29 12 min mixing | 6.00 18 min mixing | 0.97 8 min mixing | 4.15 18 min mixing | 7.00 18 min mixing | 0.93 8 min mixing |
| Glutopeak Data | | | | | | | | | | |
| Peak Maximum Time (sec) | — | — | — | — | — | 595 | 177 | 505 | 730 | 3775 |
| Torque Maximum (BU) | — | — | — | — | — | 43 | 36 | 43 | 40 | 53 |
| Bread Data (Pup Loaf with 180-minute Fermentation Straight Dough) | | | | | | | | | | |
| Bake Mix Time (minutes) 1st Rep | 2.6 | 3.8 | 4.4 | 5.3 | 6.7 | 9.2 | 4.2 | 7.6 | 8.5 | 5.3 |
| Bake Mix Time (minutes) 2nd Rep | 2.3 | 3.1 | 4.3 | 4.9 | 6.1 | 8.5 | 3.4 | 7.5 | 8.4 | 5.5 |
| Bake Absorption (%, 14% mb) 1st Rep | 64.4 | 65.1 | 65.9 | 65.3 | 66.4 | 66.5 | 66.2 | 67.9 | 69.1 | 66.3 |
| Bake Absorption (%, 14% mb) 2nd Rep | 64.4 | 65.1 | 65.9 | 65.3 | 66.4 | 69.6 | 66.2 | 67.9 | 69.1 | 66.3 |
| Loaf Weight, Average (g) 1st Rep | 138.9 | 140.2 | 137.2 | 139.6 | 139.2 | 138.9 | 139.4 | 138.2 | 138.8 | 137.2 |

TABLE 4-continued

Full trial data from HRW Bx7oe Line Evaluation and Blending common HRW flour with Bx7oe flour.

| | 0 Bx7oe | 20 Bx7oe | 40 Bx7oe | 60 Bx7oe | 80 Bx7oe | 100 Bx7oe | Typical HRW wheat variety, such as Gallagher | OK15MASBx7 ARS 8-20 | OK15MASBx7 ARS 8-29 | OK15DMASBx7 ARS 6-8 |
|---|---|---|---|---|---|---|---|---|---|---|
| Loaf Weight, Average (g) 2nd Rep | 140.2 | 140.0 | 138.8 | 139.3 | 139.0 | 137.6 | 139.3 | 138.6 | 139.2 | 137.4 |
| Loaf Volume, Average (cc) 1st Rep | 872 | 872 | 867 | 864 | 858 | 862 | 804 | 802 | 774 | 930 |
| Loaf Volume, Average (cc) 2nd Rep | 850 | 838 | 845 | 888 | 854 | 844 | 820 | 801 | 790 | 954 |
| Specific Volume, Average (cc/g) 1st Rep | 6.28 | 6.22 | 6.32 | 6.19 | 6.16 | 6.21 | 5.77 | 5.80 | 5.58 | 6.78 |
| Specific Volume, Average (cc/g) 2nd Rep | 6.06 | 5.99 | 6.09 | 6.37 | 6.14 | 6.13 | 5.89 | 5.78 | 5.68 | 6.94 |
| Bread Score | | | | | | | | | | |
| Internal Grain, Texture, Color (1-10) 1st Rep | 6.8 | 7.0 | 7.0 | 7.0 | 7.0 | 6.5 | 7.0 | 7.0 | 6.0 | 6.8 |
| Internal Grain, Texture, Color (1-10) 2nd Rep | 6.0 | 6.0 | 6.8 | 6.0 | 6.0 | 6.8 | 6.5 | 6.8 | 6.0 | 5.8 |

Further Embodiments

In an embodiment, the disclosure provides a composition comprising a seed of OK15MASBx7 ARS 8-29 comprised in plant seed growth media. Advantageously, plant seed growth media can provide adequate physical support for seeds and can retain moisture and/or nutritional components. In certain embodiments, the plant seed growth media is a soil or synthetic cultivation medium. Any plant seed growth media known in the art may be utilized in this embodiment and the disclosure is in no way limited to soil or synthetic cultivation medium. Examples of characteristics for soils that may be desirable in certain embodiments can be found, for instance, in U.S. Pat. Nos. 3,932,166 and 4,707,176. Plant cultivation media are well known in the art and may, in certain embodiments, comprise polymers, hydrogels, or the like. Examples of such compositions are described, for example, in U.S. Pat. No. 4,241,537. In specific embodiments, the growth medium may be comprised in a container or may, for example, be soil in a field.

The disclosure provides methods and compositions relating to plants, seeds and derivatives of a new wheat variety herein referred to as OK15MASBx7 ARS 8-29.

There are numerous steps in the development of any novel plant with desirable characteristics. Selection of traits is a very important aspect of plant breeding. Once desirable traits are identified, the plants with those desirable traits are crossed in order to recombine the desirable traits and through selection, varieties or parent lines are developed. Choice of breeding or selection methods depends on the mode of plant reproduction, the heritability of the trait(s) being improved, and the type of variety used commercially (e.g., F1 hybrid, pureline, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach is used extensively for breeding, for example, disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Pedigree breeding is used commonly for the improvement of self-pollinating crops or inbred lines of cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new varieties.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous variety or line that is the recurrent parent. The source of the trait to be transferred is called the donor parent. The resulting plant is expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. SSR technology is currently the most efficient and practical marker technology; more marker loci may be routinely used and more alleles per marker locus may be found using SSRs in comparison to RFLPs. SNPs may also be used to identify the unique genetic composition of the disclosure and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent. This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into wheat varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of double haploids may also be used for the development of homozygous lines in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

This disclosure also is directed to methods for producing a wheat plant by crossing a first parent wheat plant with a second parent wheat plant wherein either the first or second parent wheat plant is a wheat plant of the variety OK15MASBx7 ARS 8-29. Further, both first and second parent wheat plants can come from the variety OK15MASBx7 ARS 8-29. Still further, this disclosure also is directed to methods for producing a OK15MASBx7 ARS 8-29-derived wheat plant by crossing variety OK15MASBx7 ARS 8-29 with a second wheat plant and growing the progeny seed and repeating the crossing and growing steps with the OK15MASBx7 ARS 8-29-derived plant from 0 to 7 times. Thus, any such methods using the variety OK15MASBx7 ARS 8-29 are part of this disclosure: selfing, backcrosses, hybrid production, crosses to populations, and the like. All plants produced using variety OK15MASBx7 ARS 8-29 as a parent are within the scope of this disclosure, including plants derived from variety OK15MASBx7 ARS 8-29. Advantageously, the variety may be used in crosses with other, different, varieties to produce first generation ($F_1$) wheat seeds and plants with superior characteristics.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. In some embodiments, a transgenic variant of wheat variety OK15MASBx7 ARS 8-29 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last 15 to 20 years several methods for producing transgenic plants have been developed, and the present disclosure also relates to transgenic variants of wheat variety OK15MASBx7 ARS 8-29.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least approximately 1000 nucleotides of sequence upstream from the 5' end of the coding region and at least approximately 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the disclosure may be produced by any means, including genomic preparations, cDNA preparations, in vitro synthesis, RT-PCR, and in vitro or in vivo transcription.

One embodiment of the disclosure is a process for producing wheat variety OK15MASBx7 ARS 8-29 further comprising a desired trait, the process comprising introducing a transgene that confers a desired trait to a wheat plant of variety OK15MASBx7 ARS 8-29. In certain embodiments, the desired trait may be one or more of herbicide tolerance or resistance, insect resistance or tolerance, disease resistance or tolerance, resistance for bacterial, viral, or fungal disease, male fertility, male sterility, decreased phytate, or modified fatty acid or carbohydrate metabolism. The specific transgene may be any known in the art or listed herein, including, but not limited to a polynucleotide conferring resistance to imidazolinone, dicamba, sulfonylurea, glyphosate, glufosinate, triazine, benzonitrile, cyclohexanedione, phenoxy propionic acid, and L-phosphinothricin; a polynucleotide encoding a *Bacillus thuringiensis* polypeptide, a polynucleotide encoding phytase, FAD-2, FAD-3, galactinol synthase or a raffinose synthetic enzyme, *Fusarium, Septoria*, or various viruses or bacteria. In other embodiments, the genetic element may introduce a nucleic acid molecule including one that encodes a protein that in itself has value in industrial, pharmaceutical or other commercial or research uses.

Numerous methods for plant transformation have been developed, including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," *Maydica,* 44:101-109 (1999). In addition, expression vectors and in vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular wheat plant may then be moved into the genome of another variety using traditional breeding techniques that are well known in the plant breeding arts. For example, a backcrossing approach is used to move a transgene from a transformed wheat variety into an already developed wheat variety, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Included among various plant transformation techniques are methods that permit the site-specific modification of a plant genome, including coding sequences, regulatory elements, non-coding and other DNA sequences in a plant genome. Such methods are well-known in the art and include, for example, use of the CRISPR-Cas system, zinc-finger nucleases (ZFNs), and transcription activator-like effector nucleases (TALENs), among others.

Expression Vectors

Plant transformation may involve the construction of an expression vector which will function in plant cells. Such a vector can comprise DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed wheat plants using transformation methods as described below to incorporate transgenes into the genetic material of the wheat plant(s).

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.,* 86:1216 (1988); Jones et al., *Mol. Gen. Genet.,* 210:86 (1987); Svab et al., *Plant Mol. Biol.,* 14:197 (1990); Hille et al., *Plant Mol. Biol.,* 7:171 (1986)). Other selectable marker genes confer resistance to herbicides such as glyphosate, glufosinate, or bromoxynil (Comai et al., *Nature,* 317:741-744 (1985); Gordon-Kamm et al., *Plant Cell,* 2:603-618 (1990); Stalke et al., *Science,* 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz et al., *Somatic Cell Mol. Genet.,* 13:67 (1987); Shah et al., *Science,* 233:478 (1986); Charest et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri et al., *EMBO J.,* 8:343 (1989); Koncz et al., *Proc. Natl. Acad. Sci. USA,* 84:131 (1987); DeBlock et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway et al., *J. Cell Biol.,* 115:151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science,* 263:802 (1994)). GFP and mutants of GFP may be used as screenable markers.

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in wheat. Optionally, the inducible promoter is operably linked to a nucleotide sequence encoding a signal sequence which is operably linked to a gene for expression in wheat. With an inducible promoter the rate of transcription increases in response to an inducing agent.

Any inducible promoter can be used. See, Ward et al., *Plant Mol. Biol.,* 22:361-366 (1993). Exemplary inducible promoters include, but are not limited to, that from the ACEI system which responds to copper (Mett et al., *Proc. Natl. Acad. Sci. USA,* 90:4567-4571 (1993)); In2 gene from maize which responds to benzenesulfonamide herbicide safeners (Hershey et al., *Mol. Gen Genetics,* 227:229-237 (1991); Gatz et al., *Mol. Gen. Genetics,* 243:32-38 (1994)); or Tet repressor from Tn10 (Gatz et al., *Mol. Gen. Genetics,* 227:229-237 (1991)). A particularly preferred inducible promoter is a promoter that responds to an inducing agent to which plants do not normally respond. An exemplary inducible promoter is the inducible promoter from a steroid hormone gene, glucocorticoid response elements, the transcriptional activity of which is induced by a glucocorticoid hormone (Schena et al., *Proc. Natl. Acad. Sci. USA,* 88:10421-10425 (1991)).

B. Constitutive Promoters—A constitutive promoter is operably linked to a gene for expression in wheat or the constitutive promoter is operably linked to a nucleotide sequence encoding a signal sequence which is operably linked to a gene for expression in wheat.

Many different constitutive promoters can be utilized. Exemplary constitutive promoters include, but are not limited to, the promoters from plant viruses such as the 35S promoter from CaMV (Odell et al., *Nature,* 313:810-812 (1985)) and the promoters from such genes as rice actin (McElroy et al., *Plant Cell,* 2: 163-171 (1990)); ubiquitin (Christensen et al., *Plant Mol. Biol.,* 12:619-632 (1989);

Christensen et al., *Plant Mol. Biol.,* 18:675-689 (1992)); pEMU (Last et al., *Theor. Appl. Genet.,* 81:581-588 (1991)); MAS (Velten et al., *EMBO J.,* 3:2723-2730 (1984)); and maize H3 histone (Lepetit et al., *Mol. Gen. Genetics,* 231: 276-285 (1992); Atanassova et al., *Plant Journal,* 2 (3): 291-300 (1992)). The ALS promoter, an Xba1/Nco1 fragment 5' to the *Brassica napus* ALS3 structural gene (or a nucleotide sequence similarity to said Xba1/Nco1 fragment), represents a particularly useful constitutive promoter. See PCT Application WO 96/30530.

C. Tissue-Specific or Tissue-Preferred Promoters—A tissue-specific promoter is operably linked to a gene for expression in wheat. Optionally, the tissue-specific promoter is operably linked to a nucleotide sequence encoding a signal sequence which is operably linked to a gene for expression in wheat. Plants transformed with a gene of interest operably linked to a tissue-specific promoter produce the protein product of the transgene exclusively, or preferentially, in a specific tissue.

Any tissue-specific or tissue-preferred promoter can be utilized. Exemplary tissue-specific or tissue-preferred promoters include, but are not limited to, a root-preferred promoter such as that from the phaseolin gene (Murai et al., *Science,* 23:476-482 (1983); Sengupta-Gopalan et al., *Proc. Natl. Acad. Sci. USA,* 82:3320-3324 (1985)); a leaf-specific and light-induced promoter such as that from cab or rubisco (Simpson et al., *EMBO J.,* 4(11): 2723-2729 (1985); Timko et al., *Nature,* 318:579-582 (1985)); an anther-specific promoter such as that from LAT52 (Twell et al., *Mol. Gen. Genetics,* 217:240-245 (1989)); a pollen-specific promoter such as that from Zm13 (Guerrero et al., *Mol. Gen. Genetics,* 244:161-168 (1993)); or a microspore-preferred promoter such as that from apg (Twell et al., *Sex. Plant Reprod.,* 6:217-224 (1993)).

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.,* 20:49 (1992); Knox, C. et al., *Plant Mol. Biol.,* 9:3-17 (1987); Lerner et al., *Plant Physiol.,* 91:124-129 (1989); Frontes et al., *Plant Cell,* 3:483-496 (1991); Matsuoka et al., *Proc. Natl. Acad. Sci.,* 88:834 (1991); Gould et al., *J. Cell. Biol.,* 108:1657 (1989); Creissen et al., *Plant J.,* 2:129 (1991); Kalderon et al., *Cell,* 39:499-509 (1984); Steifel et al., *Plant Cell,* 2:785-793 (1990).

Agronomic Genes

By means of the present disclosure, wheat plants can be genetically engineered or modified to express various phenotypes of agronomic interest. Through the transformation of wheat, the expression of genes can be altered to enhance disease resistance, insect resistance, herbicide resistance, agronomic, grain quality, and other traits. DNA sequences native to wheat, as well as non-native DNA sequences, can be transformed into wheat and used to alter levels of native or non-native proteins. Various promoters, targeting sequences, enhancing sequences, and other DNA sequences can be inserted into the genome for the purpose of altering the expression of proteins. Reduction of the expression or activity of specific genes is desirable for several aspects of genetic engineering in plants. Suppression of endogenous wheat gene expression can be affected by a variety of techniques including, but not limited to, loss-of-function mutations in endogenous genes, with transgenes, or by using gene-editing or mutagenesis-mediated genome rearrangements.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy et al., *PNAS USA,* 85:8805-8809 (1988); and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan et al., *Bio/Technology,* 12:883-888 (1994); Neuhuber et al., *Mol. Gen. Genet.,* 244:230-241 (1994)); RNA interference (Napoli et al., *Plant Cell,* 2:279-289 (1990); U.S. Pat. No. 5,034,323; Sharp, Genes Dev., 13:139-141 (1999); Zamore et al., *Cell,* 101:25-33 (2000); Montgomery et al., *PNAS USA,* 95:15502-15507 (1998)), virus-induced gene silencing (Burton et al., *Plant Cell,* 12:691-705 (2000); Baulcombe, *Curr. Op. Plant Bio.,* 2:109-113 (1999)); target-RNA-specific ribozymes (Haseloff et al., *Nature,* 334: 585-591 (1988)); hairpin structures (Smith et al., *Nature,* 407:319-320 (2000); WO 99/53050; WO 98/53083); MicroRNA (Aukerman & Sakai, *Plant Cell,* 15:2730-2741 (2003)); ribozymes (Steinecke et al., *EMBO J.,* 11:1525 (1992); Perriman et al., *Antisense Res. Dev.,* 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Exemplary transgenes or modified genes include, but are not limited to, those categorized below:

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones et al., *Science,* 266:789 (1994) (cloning of the tomato Cf-9 gene for resistance to *Cladosporium flavum*); Martin et al., *Science,* 262:1432 (1993) (tomato Pto gene for resistance to *Pseudomonas syringae* pv. tomato encodes a protein kinase); Mindrinos et al., *Cell,* 78:1089 (1994) (*Arabidopsis* RSP2 gene for resistance to *Pseudomonas syringae*); McDowell & Woffenden, *Trends Biotechnol.,* 21(4): 178-83 (2003); and Toyoda et al., *Transgenic Res.,* 11 (6):567-82 (2002).

(B) A *Bacillus thuringiensis* protein, a derivative thereof or a synthetic polypeptide modelled thereon. See, for example, Geiser et al., *Gene,* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

(C) A lectin. See, for example, Van Damme et al., *Plant Molec. Biol.,* 24:25 (1994), who disclose the nucleotide sequences of several *Clivia miniata* mannose-binding lectin genes.

(D) A vitamin-binding protein such as avidin. See, PCT Application US 93/06487, which teaches the use of avidin and avidin homologues as larvicides against insect pests.

(E) An enzyme inhibitor, for example, a protease or proteinase inhibitor or an amylase inhibitor. See, for example, Abe et al., *J. Biol. Chem.,* 262: 16793 (1987) (nucleotide sequence of rice cysteine proteinase inhibitor); Huub et al., *Plant Molec. Biol.,* 21:985 (1993) (nucleotide sequence of cDNA encoding tobacco proteinase inhibitor I); Sumitani et al., *Biosci. Biotech. Biochem.,* 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

(F) An insect-specific hormone or pheromone, such as an ecdysteroid or juvenile hormone, a variant thereof, a mimetic based thereon, or an antagonist or agonist thereof. See, for example, the disclosure by Hammock et al., *Nature,* 344:458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.,* 269:9 (1994) (expression cloning yields DNA coding for insect diuretic hormone receptor); Pratt et al., *Biochem. Biophys. Res. Comm.,* 163:1243 (1989) (an allostatin is identified in *Diploptera puntata*); Chattopadhyay et al., *Critical Reviews in Microbiology,* 30(1):33-54 (2004); Zjawiony, *J Nat Prod,* 67(2):300-310 (2004); Carlini & Grossi-de-Sa, *Toxicon,* 40(11): 1515-1539 (2002); Ussuf et al., *Curr Sci.,* 80(7):847-853 (2001); Vasconcelos & Oliveira, *Toxicon,* 44(4):385-403 (2004). See also, U.S. Pat. No. 5,266,317 to Tomalski et al., which discloses genes encoding insect-specific, paralytic neurotoxins.

(H) An insect-specific venom produced in nature by a snake, a wasp, etc. For example, see, Pang et al., *Gene,* 116:165 (1992), for disclosure of heterologous expression in plants of a gene coding for a scorpion insectotoxic peptide.

(I) An enzyme responsible for a hyperaccumulation of a monoterpene, a sesquiterpene, a steroid, hydroxamic acid, a phenylpropanoid derivative, or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also, Kramer et al., *Insect Biochem. Molec. Biol.,* 23:691 (1993), who teach the nucleotide sequence of a cDNA encoding tobacco hornworm chitinase, and Kawalleck et al., *Plant Molec. Biol.,* 21:673 (1993), who provide the nucleotide sequence of the parsley ubi4-2 polyubiquitin gene, U.S. Pat. Nos. 7,145,060, 7,087,810, and 6,563,020.

(K) A molecule that stimulates signal transduction. For example, see the disclosure by Botella et al., *Plant Molec. Biol.,* 24:757 (1994), of nucleotide sequences for mung bean calmodulin cDNA clones, and Griess et al., *Plant Physiol.,* 104:1467 (1994), who provide the nucleotide sequence of a maize calmodulin cDNA clone.

(L) A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

(M) A membrane permease, a channel former or a channel blocker. For example, see the disclosure of Jaynes et al., *Plant Sci,* 89:43 (1993), of heterologous expression of a cecropin-β lytic peptide analog to render transgenic tobacco plants resistant to *Pseudomonas solanacearum.*

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy et al., *Ann. Rev. Phytopathol.,* 28:451 (1990). Coat protein-mediated resistance has been conferred upon transformed plants against alfalfa mosaic virus, cucumber mosaic virus, and tobacco mosaic virus.

(O) An insect-specific antibody or an immunotoxin derived therefrom. Thus, an antibody targeted to a critical metabolic function in the insect gut would inactivate an affected enzyme, killing the insect. See, Taylor et al., Abstract #497, Seventh Int'l Symposium on Molecular Plant-Microbe Interactions (Edinburgh, Scotland 1994) (enzymatic inactivation in transgenic tobacco via production of single-chain antibody fragments).

(P) A virus-specific antibody. See, for example, Tavladoraki et al., *Nature,* 366:469 (1993), who show that transgenic plants expressing recombinant antibody genes are protected from virus attack.

(Q) A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See, Lamb et al., *Bio/Technology,* 10:1436 (1992). The cloning and characterization of a gene which encodes a bean endopolygalacturonase-inhibiting protein is described by Toubart et al., *Plant J.,* 2:367 (1992).

(R) A developmental-arrestive protein produced in nature by a plant. For example, Logemann et al., *Bio/Technology,* 10:305 (1992), have shown that transgenic plants expressing the barley ribosome-inactivating gene have an increased resistance to fungal disease.

(S) Genes involved in the Systemic Acquired Resistance (SAR) Response and/or the pathogenesis-related genes. Briggs, S., *Current Biology,* 5(2) (1995); Pieterse & Van Loon, *Curr. Opin. Plant Bio.,* 7(4):456-64 (2004); and Somssich, Cell, 113(7):815-6 (2003).

(T) Antifungal genes. Genes expressing proteins with antifungal action. *Fusarium* head blight along with deoxynivalenol both produced by the pathogen *Fusarium graminearum* (Schwabe) have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome-inactivating proteins, flavonoids, and lactoferricin. During infection with *Fusarium graminearum,* deoxynivalenol is produced. There is evidence that production of deoxynivalenol increases the virulence of the disease. Genes with properties for detoxification of deoxynivalenol have been engineered for use in wheat. A synthetic peptide that competes with deoxynivalenol has been identified. Changing the ribosomes of the host so that they have reduced affinity for deoxynivalenol has also been used to reduce the virulence of *Fusarium graminearum*. Genes used to help reduce *Fusarium* head blight include, but are not limited to, Tri101 (*Fusarium*), PDR5 (yeast), tlp-1 (oat), tlp-2 (oat), leaf tlp-1 (wheat), tlp (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tlp (*Arabidopsis*), zeamatin (maize), type 1 RIP (barley), NPR1 (*Arabidopsis*), lactoferrin (mammal), oxalylCoA-decarboxylase (bacterium), IAP (baculovirus), ced-9 (*C. elegans*), and glucanase (rice and barley).

(U) A gene, for example, the H9, H10, and H21 genes, conferring resistance to a pest, such as Hessian fly, stem soft fly, cereal leaf beetle, and/or green bug.

(V) Defensin genes. See, WO 03/000863 and U.S. Pat. No. 6,911,577.

(W) A gene conferring resistance to diseases such as wheat rusts, *Septoria tritici, Septoria nodorum*, powdery mildew, *Helminthosporium* diseases, smuts, bunts, *Fusarium* diseases, bacterial diseases, and viral diseases.

(X) Cystatin and cysteine proteinase inhibitors.

Any of the above-listed disease or pest resistance genes can be introduced into the claimed wheat variety through a variety of means including, but not limited to, transformation and crossing.

2. Genes that Confer Resistance to an Herbicide, for Example:

(A) An herbicide that inhibits the growing point or meristem, such as an imidazolinone or a sulfonylurea. Exemplary genes in this category code for mutant ALS and AHAS enzyme as described, for example, by Lee et al., *EMBO J.,* 7:1241 (1988) and Miki et al., *Theor. Appl. Genet.,* 80:449 (1990), respectively.

(B) Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy propionic acids, and cyclohexanediones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al., also describes genes encoding EPSPS enzymes. See also, U.S. Pat. Nos. 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, and 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada et al. and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans et al. DeGree F. et al., *Bio/Technology,* 7:61 (1989) describe the production of transgenic plants that express chimeric bar genes coding for phosphinothricin acetyl transferase activity. Exemplary of genes conferring resistance to phenoxy propionic acids and cyclohexanediones, such as sethoxydim and haloxyfop are the Acc1-S1, Acc1-S2, and Acc2-S3 genes described by Marshall et al., *Theor. Appl. Genet.,* 83:435 (1992).

(C) An herbicide that inhibits photosynthesis, such as a triazine (psbA and gs+ genes) and a benzonitrile (nitrilase gene). Przibila et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes et al., *Biochem. J.,* 285:173 (1992).

(D) Acetohydroxy acid synthase, which has been found to make plants that express this enzyme resistant to multiple types of herbicides, has been introduced into a variety of plants. See, Hattori et al., *Mol. Gen. Genet.,* 246:419 (1995). Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17 (1994)); genes for glutathione reductase and superoxide dismutase (Aono et al., *Plant Cell Physiol.,* 36:1687 (1995)); and genes for various phosphotransferases (Datta et al., *Plant Mol. Biol.,* 20:619 (1992)).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes can be introduced into the claimed wheat variety through a variety of means including but not limited to transformation and crossing.

3. Genes that Confer or Contribute to an Altered Grain Characteristic, Such as:

(A) Altered fatty acids, for example, by (1) down-regulation of stearoyl-ACP desaturase to increase stearic acid content of the plant. See, WO99/64579, (2) elevating oleic acid via FAD-2 gene modification and/or decreasing linolenic acid via FAD-3 gene modification, See, U.S. Pat. Nos. 6,063,947; 6,323,392; 6,372,965 and WO 93/11245, (3) altering conjugated linolenic or linoleic acid content, such as in WO 01/12800, (4) altering LEC1, AGP, Dek1, Superal1, mi1ps, various Ipa genes such as Ipa1, Ipa3, hpt or hggt. For example, see WO 02/42424, WO 98/22604, WO 03/011015, U.S. Pat. Nos. 6,423,886, 6,197,561, 6,825,397, US Patent Application Publication Nos. 2003/0079247, 2003/0204870, WO02/057439, WO03/011015.

(B) Altered phytate content, for example, by the (1) introduction of a phytase-encoding gene would enhance breakdown of phytate, adding more free phosphate to the transformed plant, such as for example, using an *Aspergillus niger* phytase gene, (2) up-regulation of a gene that reduces phytate content.

(C) Altered carbohydrates effected, for example, by altering a gene for an enzyme that affects the branching pattern of starch, a gene altering thioredoxin. (See, U.S. Pat. No. 6,531,648). Exemplary genes include those encoding fructosyltransferase, levansucrase, alpha-amylase, invertase, branching enzyme II, UDP-D-xylose 4-epimerase, Fragile 1 and 2, Ref1, HCHL (4-hydroxycinnamoyl-CoA hydratase/lyase), C4H (cinnamate 4-hydroxylase), AGP (ADPglucose pyrophosphorylase). The fatty acid modification genes may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication No. 2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication No. 2003/0163838, US Patent Application Publication No. 2003/0150014, US Patent Application Publication No. 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication No. 2004/0025203 (UDPGdH), U.S. Pat. No. 6,194,638 (RGP).

(F) Elevated oleic acid via FAD-2 gene modification and/or decreased linolenic acid via FAD-3 gene modification.

(G) Altering conjugated linolenic or linoleic acid content, or LEC1, AGP, Dek1, Superal1, mi1ps, various Ipa genes such as Ipa1, Ipa3, hpt, or hggt.

(H) The content of high-molecular weight gluten subunits (HMS-GS). Genomic clones have been isolated for different subunits. For example, genomic clones have transformed wheat with genes that encode a modified HMW-GS.

(I) Increased protein metabolism, zinc and iron content, for example, by regulating the NAC gene, increasing protein metabolism by regulating the Gpc-B1 gene, or regulating glutenin and gliadin genes.

4. Genes that Control Pollination, Hybrid Seed Production or Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar et al., and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

(A) Introduction of a deacetylase gene under the control of a tapetum-specific promoter and with the application of the chemical N-Ac-PPT. See, International Publication WO 01/29237.

(B) Introduction of various stamen-specific promoters. See, International Publications WO 92/13956 and WO 92/13957.

(C) Introduction of the barnase and the barstar genes. See, Paul et al., *Plant Mol. Biol.,* 19:611-622 (1992).

Also see, U.S. Pat. No. 5,426,041 (relating to a method for the preparation of a seed of a plant comprising crossing a male sterile plant and a second plant which is male fertile), U.S. Pat. No. 6,013,859 (molecular methods of hybrid seed production) and U.S. Pat. No. 6,037,523 (use of male tissue-preferred regulatory region in mediating fertility).

5. Genes that Create a Site for Site Specific DNA Integration:

This includes the introduction of FRT sites that may be used in the FLP/FRT system and/or Lox sites that may be used in the Cre/loxP system. See, for example, Lyznik et al., Site-Specific Recombination for Genetic Engineering in Plants, *Plant Cell* Rep, 21:925-932 (2003) and WO 99/25821, which are hereby incorporated by reference. Other systems that may be used include the Gin recombinase of phage Mu (Maeser et al. (1991); Vicki Chandler, The Maize Handbook, Ch. 118 (Springer-Verlag 1994)); the Pin recombinase of *E. coli* (Enomoto et al. (1983)); and the R/RS system of the pSR1 plasmid (Araki et al. (1992)).

6. Genes that Affect Abiotic Stress Resistance:

A. Genes that affect abiotic stress resistance (including but not limited to flowering, seed development, enhancement of nitrogen utilization efficiency, altered nitrogen responsiveness, drought resistance or tolerance, cold resistance or tolerance, and salt resistance or tolerance) and increased yield under stress. For example, water use efficiency can be altered through alteration of malate. In addition, various genes, including CBF genes and transcription factors, can be effective in mitigating the negative effects of freezing, high salinity, and drought on plants, as well as conferring other positive effects on plant phenotype. Abscisic acid can be altered in plants, resulting in improved plant phenotype, such as increased yield and/or increased tolerance to abiotic stress. Cytokinin expression can be modified resulting in plants with increased stress tolerance, such as drought tolerance, and/or increased yield. Nitrogen utilization can be enhanced and/or nitrogen responsiveness can be altered. Ethylene can be altered. Plant transcription factors or transcriptional regulators of abiotic stress can also be altered.

B. Improved tolerance to water stress from drought or high salt water condition. The HVA1 protein belongs to the group 3 LEA proteins that include other members such as wheat pMA2005, cotton D-7, carrot Dc3, and rape pLEA76. These proteins are characterized by 11-mer tandem repeats of amino acid domains which may form a probable amphophilic alpha-helical structure that presents a hydrophilic surface with a hydrophobic stripe. The barley HVA1 gene and the wheat pMA2005 gene are highly similar at both the nucleotide level and predicted amino acid level. These two monocot genes are closely related to the cotton D-7 gene and carrot Dc3 gene with which they share a similar structural gene organization. There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance. Studies on several Indica varieties of rice showed that the levels of group 2 LEA proteins (also known as dehydrins) and group 3 LEA proteins in roots were significantly higher in salt-tolerant varieties compared with sensitive varieties. The barley HVA1 gene was transformed into wheat. Transformed wheat plants showed increased tolerance to water stress.

C. Improved water stress tolerance through increased mannitol levels via the bacterial mannitol-1-phosphate dehydrogenase gene. It is known to produce a plant with a genetic basis for coping with water deficit by introduction of the bacterial mannitol-1-phosphate dehydrogenase gene, mt1D, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, the growth of transgenic plants was compared to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Methods for Wheat Transformation

Numerous methods for plant transformation have been developed including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports*, 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.*, 5:27 (1987); Sanford, J. C., *Trends Biotech.*, 6:299 (1988); Klein et al., *Bio/Tech.*, 6:559-563 (1988); Sanford, J. C., *Physiol Plant*, 7:206 (1990); Klein et al., *Biotechnology*, 10:268 (1992). See also, U.S. Pat. No. 5,015,580 (Christou et al.), issued May 14, 1991 and U.S. Pat. No. 5,322,783 (Tomes et al.), issued Jun. 21, 1994.

Another method for physical delivery of DNA to plants is sonication of target cells. Zhang et al., *Bio/Technology*, 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA*, 84:3962 (1987). Direct uptake of DNA into protoplasts using $CaCl_2$)) precipitation, polyvinyl alcohol or poly-L-ornithine have also been reported. Hain et al., *Mol. Gen. Genet.*, 199:161 (1985) and Draper et al., *Plant Cell Physiol.*, 23:451 (1982). Electroporation of protoplasts and whole cells and tissues have also been described (Donn et al., In Abstracts of VII$^{th}$ International Congress on *Plant Cell* and Tissue Culture IAPTC, A2-38, p. 53 (1990); D'Halluin et al., *Plant Cell*, 4:1495-1505 (1992); and Spencer et al., *Plant Mol. Biol.*, 24:51-61 (1994)).

Following transformation of target tissues, expression of the above-described selectable marker genes allows for preferential selection of transformed cells, tissues, and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular wheat plant using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Genetic Marker Profiles

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan et al., "An Integrated Genetic Linkage Map of the Soybean Genome," *Crop Science,* 39:1464-1490 (1999) and Berry et al., "Assessing Probability of Ancestry Using Simple Sequence Repeat Profiles: Applications to Maize Inbred Lines and Soybean Varieties," *Genetics,* 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for wheat variety OK15MASBx7 ARS 8-29. In addition to being used for identification of wheat variety OK15MASBx7 ARS 8-29, and plant parts and plant cells of wheat variety OK15MASBx7 ARS 8-29, the genetic profile may be used to identify a wheat plant produced through the use of wheat variety OK15MASBx7 ARS 8-29 or to verify a pedigree for progeny plants produced through the use of wheat variety OK15MASBx7 ARS 8-29. The genetic marker profile is also useful in breeding and developing backcross conversions.

The present disclosure provides in one embodiment a wheat plant variety OK15MASBx7 ARS 8-29 characterized by molecular and physiological data obtained from the representative sample of the variety deposited with the Provasoli-Guillard National Center for Marine Algae and Microbiota (NCMA). Further provided by the disclosure is a wheat plant formed by the combination of the disclosed wheat plant or plant cell with another wheat plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by polymerase chain reaction (PCR), thereby eliminating the need for labor-intensive Southern hybridization. PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties, it is preferable if all profiles are performed in the same lab.

A genetic marker profile of wheat variety OK15MASBx7 ARS 8-29 can be used to identify plants comprising wheat variety OK15MASBx7 ARS 8-29 as a parent, since such plants will comprise the same homozygous alleles as wheat variety OK15MASBx7 ARS 8-29. Because the wheat variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of wheat variety OK15MASBx7 ARS 8-29 in their development, such as wheat variety OK15MASBx7 ARS 8-29 comprising a backcross conversion, transgene, or gene edit, may be identified by having a molecular marker profile with a high percent identity to wheat variety OK15MASBx7 ARS 8-29. Such a percent identity might be 95%, 96%, 97%, 98%, 99%, 99.5%, or 99.9% identical to wheat variety OK15MASBx7 ARS 8-29.

A genetic marker profile of wheat variety OK15MASBx7 ARS 8-29 can also be used to identify essentially derived varieties and other progeny varieties developed from the use of wheat variety OK15MASBx7 ARS 8-29, as well as cells and other plant parts thereof. Progeny plants and plant parts produced using wheat variety OK15MASBx7 ARS 8-29 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from wheat variety OK15MASBx7 ARS 8-29, as measured by either percent identity or percent similarity. Such progeny may be further characterized as being within a pedigree distance of wheat variety OK15MASBx7 ARS 8-29, such as within 1, 2, 3, 4, or 5 or less cross-pollinations to a wheat plant other than wheat variety OK15MASBx7 ARS 8-29 or a plant that has wheat variety OK15MASBx7 ARS 8-29 as a progenitor. Unique molecular profiles may be identified with other molecular tools such as SNPs and RFLPs.

Gene Conversions

When the term "wheat plant" is used in the context of the present disclosure, this also includes a gene conversion of that variety. The term gene converted plant as used herein refers to those wheat plants which are developed by a plant breeding technique called backcrossing wherein essentially all of the desired morphological and physiological characteristics of a variety are recovered in addition to the gene transferred into the line via the backcrossing technique. By "essentially all" as used herein in the context of morphological and physiological characteristics it is meant that the characteristics of a plant are recovered that are otherwise present when compared in the same environment, other than occasional variant traits that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

Backcrossing methods can be used with the present disclosure to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental wheat plant that contributes the gene for the desired characteristic is termed the nonrecurrent or donor parent. This terminology refers to the fact that the nonrecurrent parent is used one time in the backcross protocol and therefore does not recur. The parental wheat plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a wheat plant is obtained wherein essentially all of the morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent variety are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. *Gene* traits may or may not be transgenic, examples of these traits include but are not limited to, herbicide resistance, resistance for bacterial, fungal, or viral disease, insect resistance, industrial usage, yield stability, yield enhancement, male sterility, reduced seed fiber content, modified seed color, increased seed protein content, increased seed oil content, reduced seed glucosinolate content, and shatter resistance. These genes are generally inherited through the nucleus. Several of these gene traits are described in U.S. Pat. Nos. 5,777,196; 5,948,957 and 5,969,212, the disclosures of which are specifically hereby incorporated by reference.

Introduction of a New Trait or Locus into OK15MASBx7 ARS 8-29

Variety OK15MASBx7 ARS 8-29 represents a new base genetic variety into which a new locus or trait may be introduced. Direct transformation and backcrossing represent two important methods that can be used to accomplish this. The term backcross conversion and single locus conversion are used interchangeably to designate the product of a backcrossing program.

Backcross Conversions of OK15MASBx7 ARS 8-29

A backcross conversion of OK15MASBx7 ARS 8-29 occurs when DNA sequences are introduced through backcrossing, with OK15MASBx7 ARS 8-29 utilized as the recurrent parent. Both naturally occurring and transgenic DNA sequences may be introduced through backcrossing techniques. A backcross conversion may produce a plant with a trait or locus conversion in one or more backcrosses, including at least 1 cross, at least 2 crosses, at least 3 crosses, at least 4 crosses, at least 5 crosses, or additional crosses. Molecular marker assisted breeding or selection may be utilized to reduce the number of backcrosses necessary to achieve the backcross conversion. For example, a backcross conversion can be made in as few as two backcrosses.

The complexity of the backcross conversion method depends on the type of trait being transferred (single genes or closely linked genes versus unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance or tolerance (bacterial, fungal or viral), insect resistance or tolerance, and herbicide tolerance or resistance. In addition, an introgression site itself, such as an FRT site, Lox site, or other site specific integration site, may be inserted by backcrossing and utilized for direct insertion of one or more genes of interest into a specific plant variety. A single locus may contain several transgenes, such as a transgene for disease resistance that, in the same expression vector, also contains a transgene for herbicide tolerance or resistance. The gene for herbicide tolerance or resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selling the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Some sources suggest from one to four or more backcrosses, but as noted above, the number of backcrosses necessary can be reduced with the use of molecular markers. Other factors, such as a genetically similar donor parent, may also reduce the number of backcrosses necessary. Backcrossing is easiest for simply inherited, dominant, and easily selected traits.

One process for adding or modifying a trait or locus in wheat variety OK15MASBx7 ARS 8-29 comprises crossing OK15MASBx7 ARS 8-29 plants grown from OK15MASBx7 ARS 8-29 seed with plants of another wheat variety that comprise the desired trait or locus, selecting F1 progeny plants that comprise the desired trait or locus to produce selected F1 progeny plants, crossing the selected progeny plants with the OK15MASBx7 ARS 8-29 plants to produce backcross progeny plants, selecting for backcross progeny plants that have the desired trait or locus and the morphological characteristics of wheat variety OK15MASBx7 ARS 8-29 to produce selected backcross progeny plants, and backcrossing to OK15MASBx7 ARS 8-29 three or more times in succession to produce selected fourth or higher backcross progeny plants that comprise said trait or locus. The modified OK15MASBx7 ARS 8-29 may be further characterized as having essentially all of the morphological and physiological characteristics of wheat variety OK15MASBx7 ARS 8-29 listed in Table 1, as determined at the 5% significance level when grown in the same environmental conditions and/or may be characterized by percent similarity or identity to OK15MASBx7 ARS 8-29 as determined by SSR markers. The above method may be utilized with fewer backcrosses in appropriate situations, such as when the donor parent is highly related or markers are used in the selection step. Desired nucleic acids that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny wheat seed by adding a step at the end of the process that comprises crossing OK15MASBx7 ARS 8-29 with the introgressed trait or locus with a different wheat plant and harvesting the resultant first generation progeny wheat seed.

A further embodiment of the disclosure is a back-cross conversion of wheat variety OK15DMASBx7 ARS 8-29. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance or tolerance, insect resistance or tolerance, herbicide tolerance or resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are known. Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), powdery mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, and Dn5), Black stem rust resistance genes (Sr38), Yellow rust resistance genes (Yr series such as Yr 1, YrSD, Yrsu, Yrl7, Yrl5, and YrH52), aluminum tolerance genes (Alt(BH)), dwarf genes (Rht), vernalization genes (Vrn), Hessian fly resistance genes (H9, H10, H21, and H29), grain color genes (R/r), glyphosate resistance genes (EPSPS), glufosinate genes (bar, pat) and water stress tolerance genes (Hva 1 and mt1D). The trait of interest is transferred from the donor parent to the recurrent parent, which in this case is the wheat plant disclosed herein, OK15DMASBx7 ARS 8-29OK15MASBx7 ARS 8-29. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Using OK15MASBx7 ARS 8-29 to Develop Other Wheat Varieties

Wheat varieties such as OK15MASBx7 ARS 8-29 are typically developed for use in seed and grain production. However, wheat varieties such as OK15MASBx7 ARS 8-29 also provide a source of breeding material that may be used to develop new wheat varieties. Plant breeding techniques known in the art and used in a wheat plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often, combinations of these techniques are used. The development of wheat varieties in a plant breeding program requires, in general, the development and evaluation of homozygous varieties. There are many analytical methods available to evaluate a new variety. The oldest and most traditional method of analysis is the observation of phenotypic traits but genotypic analysis is often used.

TILLING

TILLING (Targeting Induced Local Lesions IN Genomes) can be used to produce plants in which endogenous genes comprise a mutation. In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time. For a TILLING assay, heteroduplex methods using specific endonucleases can be used to detect single nucleotide polymorphisms (SNPs). Alternatively, Next Generation Sequencing of DNA from pools of mutagenized plants can be used to identify mutants in the gene of choice. Typically, a mutation frequency of one mutant per 1000 plants in the mutagenized population is achieved. Using this approach, many thousands of plants can be screened to identify any individual with a single base change as well as small insertions or deletions (1-30 bp) in any gene or specific region of the genome. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Genome Editing

Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption. Engineered nucleases useful in the methods of the present disclosure include zinc finger nucleases (ZFNs), transcription activator-like (TAL) effector nucleases (TALEN) and CRISPR Cas9 type nucleases.

Typically, nuclease encoded genes are delivered into cells by plasmid DNA, viral vectors or in vitro transcribed mRNA. A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the Cis2His2 type of zinc finger that is very generally represented, for example, by the zinc finger transcription factors TFIIIA or Sp1. In a preferred embodiment, the zinc finger domain comprises three Cis2His2 type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques (see, for example, Bibikova et al., 2002).

The ZFN DNA-cleavage domain is derived from a class of non-specific DNA cleavage domains, for example the DNA-cleavage domain of a Type II restriction enzyme such as Fold (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain. TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AhvI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Distinct from the site-specific nucleases described above, the clustered regulatory interspaced short palindromic repeats (CRISPR)/Cas system provides an alternative to ZFNs and TALENs for inducing targeted genetic alterations, via RNA-guided DNA cleavage.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

Tissue Culture

Further reproduction of the variety can occur by tissue culture and regeneration. Tissue culture of various tissues and regeneration of plants therefrom is well known and widely published. For example, reference may be had to Komatsuda, T. et al., *Crop Sci.,* 31:333-337 (1991); Stephens, P. A. et al., *Theor. Appl. Genet.,* 82:633-635 (1991); Komatsuda, T. et al., *Plant Cell, Tissue and Organ Culture,* 28:103-113 (1992); Dhir, S. et al., *Plant Cell Reports,* 11:285-289 (1992); Pandey, P. et al., *Japan J. Breed.,* 42:1-5 (1992); and Shetty, K. et al., *Plant Science,* 81:245-251

(1992); as well as U.S. Pat. No. 5,024,944, issued Jun. 18, 1991 to Collins et al. and U.S. Pat. No. 5,008,200, issued Apr. 16, 1991 to Ranch et al. Thus, another embodiment of this disclosure is to provide cells which upon growth and differentiation produce wheat plants having the morphological and physiological characteristics of wheat variety OK15MASBx7 ARS 8-29.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Also provided are methods for vegetatively propagating a plant wheat variety OK15MASBx7 ARS 8-29. In one embodiment, vegetatively propagating can be interchangeably used with vegetative reproduction. In some embodiments, the methods comprise collecting a part of a wheat variety OK15MASBx7 ARS 8-29 and regenerating a plant from said part. In some embodiments, the part can be for example a leaf cutting that is rooted into an appropriate medium according to techniques known by the one skilled in the art. Plants, plant parts and seeds thereof produced by such methods are also included in the present embodiments. In another aspect, the plants thereof produced by such methods have all the physiological and morphological characteristics of wheat variety OK15MASBx7 ARS 8-29 listed in Table 1, including but not limited to as determined at the 5% significance level when grown in the same environmental conditions. In some embodiments, plants produced by such methods consist of one, more than one, or all physiological and morphological characteristics of wheat variety OK15MASBx7 ARS 8-29 listed in Table 1, including but not limited to as determined at the 5% significance level when grown in the same environmental conditions.

Additional Breeding Methods

This disclosure is directed to methods for producing a wheat plant by crossing a first parent wheat plant with a second parent wheat plant wherein either the first or second parent wheat plant is variety OK15MASBx7 ARS 8-29. The other parent may be any other wheat plant. Any such methods using wheat variety OK15MASBx7 ARS 8-29 are part of this disclosure: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, Principles of Plant Breeding (1960); Simmonds, Principles of Crop Improvement (1979); Sneep et al. (1979); Fehr, "Breeding Methods for Cultivar Development," Chapter 7, Soybean Improvement, Production and Uses, 2nd ed., Wilcox editor (1987)).

The following describes breeding methods that may be used with wheat variety OK15MASBx7 ARS 8-29 in the development of further wheat plants. One such embodiment is a method for developing a variety OK15MASBx7 ARS 8-29 progeny wheat plant in a wheat plant breeding program comprising: obtaining the wheat plant, or a part thereof, of variety OK15MASBx7 ARS 8-29, utilizing the plant, or plant part, as a source of breeding material, and selecting a wheat variety OK15MASBx7 ARS 8-29 progeny plant with molecular markers in common with variety OK15MASBx7 ARS 8-29 and/or with morphological and/or physiological characteristics selected from the characteristics listed in Table 1. Breeding steps that may be used in the wheat plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of wheat variety OK15MASBx7 ARS 8-29 progeny wheat plants, comprising crossing variety OK15MASBx7 ARS 8-29 with another wheat plant, thereby producing a population of wheat plants which, on average, derive 50% of their alleles from wheat variety OK15MASBx7 ARS 8-29. A plant of this population will have desirable individuals that can be selected and repeatedly selfed or sibbed with a wheat variety resulting from these successive filial generations. One embodiment of this disclosure is the wheat variety produced by this method and that has obtained at least 50% of its alleles from wheat variety OK15MASBx7 ARS 8-29.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus, the disclosure includes wheat variety OK15MASBx7 ARS 8-29 progeny plants comprising a combination of at least two variety OK15MASBx7 ARS 8-29 traits selected from those listed in Table 1, so that the progeny plant is not significantly different for the traits than wheat variety OK15MASBx7 ARS 8-29 as determined at the 5% significance level when grown in the same environmental conditions. Using techniques described herein, molecular markers may be used to identify the progeny plant as a wheat variety OK15MASBx7 ARS 8-29 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of wheat variety OK15MASBx7 ARS 8-29 may also be characterized through their filial relationship with wheat variety OK15MASBx7 ARS 8-29, as for example, being within a certain number of breeding crosses of wheat variety OK15MASBx7 ARS 8-29. A breeding cross is a cross made to introduce new genetics into the progeny, and is distinguished from a cross, such as a self or a sib cross, made to select among existing genetic alleles. The lower the number of breeding crosses in the pedigree, the closer the relationship between wheat variety OK15MASBx7 ARS 8-29 and its progeny. For example, progeny produced by the methods described herein may be within 1, 2, 3, 4, or 5 breeding crosses of wheat variety OK15MASBx7 ARS 8-29.

Seed Treatments and Cleaning

Methods of harvesting the seed of the wheat variety OK15MASBx7 ARS 8-29 as seed for planting are provided. Embodiments include cleaning the seed, treating the seed, and/or conditioning the seed. Cleaning the seed is understood in the art to include removal of foreign debris such as one or more of weed seed, chaff, and plant matter, from the seed. Conditioning the seed is understood in the art to include controlling the temperature and rate of dry down of the seed and storing seed in a controlled temperature environment. Seed treatment is the application of a composition to the surface of the seed such as a coating or powder. Methods for producing a treated seed include the step of applying a composition to the seed or seed surface. Seeds are provided which have on the surface a composition. Biological active components such as bacteria can also be used as a seed treatment. Some examples of compositions are insecticides, fungicides, pesticides, antimicrobials, germination inhibitors, germination promoters, cytokinins, and nutrients.

Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB (EPA registration number 00293500419, containing quintozen and terrazole), penflufen, *penicillium*, penthiopyrad, permethrine, picoxystrobin, prothioconazole, pyraclostrobin, rynaxypyr, S-metolachlor, saponin, sedaxane, TCMTB (2-(thiocyanomethylthio) benzothiazole), tebuconazole, thiabendazole, thiamethoxam, thiocarb, thiram, tolclofos-methyl, triadimenol, *trichoderma*, trifloxystrobin, triticonazole and/or zinc.

Methods of milling the seed of wheat variety OK15MASBx7 ARS 8-29 and the flour produced from such milling are provided. The flour may include a cell of wheat variety OK15MASBx7 ARS 8-29.

Another embodiment includes producing a commodity plant product comprising collecting the commodity plant product from the plant of wheat variety OK15MASBx7 ARS 8-29. Another embodiment provides for the commodity plant products produced includes but is not limited to grain, flour, baked goods, cereals, pasta, beverages, livestock feed, straw, construction materials, and starches.

While a number of exemplary aspects and embodiments have been discussed above, those of skill in the art will that certain changes and modifications such as single gene modifications and mutations, somoclonal variants, variant individuals selected from large populations of the plants of the instant variety and the like may be practiced within the scope of the disclosure, as limited only by the scope of the appended claims All references, including publications, patents, and patent applications, cited herein are hereby incorporated by reference to the same extent as if each reference were individually and specifically indicated to be incorporated by reference and were set forth in its entirety herein.

Deposit

A deposit of the seed of wheat plant OK15MASBx7 ARS 8-29 is and has been maintained by Oklahoma State University, 1201 Innovation Way Drive, Suite 210, Stillwater, OK 74074, since prior to the filing date of this application. Access to this deposit will be available during the pendency of the application to the Commissioner of Patents and Trademarks and persons determined thereby to be entitled thereto upon request. Deposit will be made in a timely manner upon allowance of any claims in the application, whereby, the Applicant(s) will make available to the public, pursuant to 37 CFR 1.808(2), a deposit of at least 625 seeds of variety OK15MASBx7 ARS 8-29 with the Provasoli-Guillard National Center for Marine Algae and Microbiota (NCMA), 60 Bigelow Drive, East Boothbay, ME 04544, USA, with NCMA Accession No. 202604023. The seeds deposited with the NCMA on Apr. 3, 2026 will be taken from the same deposit maintained at Oklahoma State University and described above. Additionally, Applicant(s) will meet all the requirements of 37 C.F.R. § 1.801-1.809, including providing an indication of the viability of the sample when the deposit is made. These deposits will be maintained in the NCMA depository, which is a public depository, for a period of 30 years, or 5 years after the most recent request, or for the enforceable life of the patent, whichever is longer, and will be replaced if it ever becomes nonviable during that period. Applicant has no authority to waive any restrictions imposed by law on the transfer of biological material or its transportation in commerce. Applicant does not waive any infringement of its rights granted under this patent or under the Plant Variety Protection Act (7 USC 2321 et seq.).

What is claimed is:

1. A commercially elite Hard Red Winter (HRW) wheat variety, wherein the variety is wheat variety OK15MASBx7 ARS 8-29, wherein a representative sample of seed of said variety has been deposited under NCMA Accession No. 202604023.

2. The wheat variety of claim 1, wherein the wheat variety has increased dough strength, as compared to typical HRW wheat varieties, and wherein the increased dough strength is due, in part, to overexpression of the wheat Bx7subunit (Bx7oe).

3. The wheat variety of claim 2, wherein dough strength is measured by mixing stability time and/or mixing tolerance index.

4. A method of producing a commodity plant product comprising collecting the commodity plant product from the plant of claim 1.

5. A wheat commodity plant product produced by the method of claim 4.

6. The wheat commodity plant product of claim 5, wherein the commodity plant product comprises at least one cell of wheat variety OK15MASBx7 ARS 8-29, wherein a representative sample of seed of said variety has been deposited under NCMA Accession No. 202604023.

7. The method of claim 4, wherein the commodity plant product is oil, meal, grain, flour, flour blends, baked goods, cereals, pasta, beverages, livestock feed, biofuel, straw, construction materials, or starches.

8. A plant of wheat variety OK15MASBx7 ARS 8-29, wherein a representative sample of seed of said variety has been deposited under NCMA Accession No. 202604023.

9. A plant part of the plant of claim 8, wherein the plant part comprises at least one cell of said plant.

10. The plant part of claim 9, selected from the group consisting of awn, leaf, pollen, ovule, embryo, cotyledon, hypocotyl, meristematic cell, root, root tip, pistil, anther, floret, seed, pericarp, spike, stem, or callus.

11. A tissue culture produced from the plant part of claim 9.

12. A wheat plant regenerated from the tissue culture of claim 11, wherein the regenerated wheat plant comprises all of the morphological and physiological characteristics of a plant grown from the wheat seed designated OK15MASBx7 ARS 8-29.

13. A wheat plant, or part thereof, having all the physiological and morphological characteristics of the wheat plant of claim 8.

14. A seed of wheat variety OK15MASBx7 ARS 8-29, wherein a representative sample of seed of said variety has been deposited under NCMA Accession No. 202604023.

15. A composition comprising the seed of claim 14 comprised in plant seed growth media, wherein a representative sample of seed of said variety has been deposited under NCMA Accession No. 202604023.

16. A method of producing wheat seed, wherein the method comprises crossing the plant of claim 8 with itself or a second wheat plant.

17. The method of claim 16, wherein the method comprises crossing the plant of wheat variety OK15MASBx7 ARS 8-29 with a second, distinct wheat plant and producing an $F_1$ hybrid seed.

18. The wheat seed produced by the method of claim 16.

19. An $F_1$ hybrid wheat plant or plant part produced by growing the seed of claim 18.

20. The method of claim 17, wherein the method further comprises: (a) crossing a plant grown from said $F_1$ hybrid seed with itself or a different wheat plant to produce a seed of a progeny plant of a subsequent generation; (b) growing a progeny plant of the subsequent generation from said seed of a progeny plant of the subsequent generation and crossing the progeny plant of the subsequent generation with itself or a second plant to produce a progeny plant of a further subsequent generation; and (c) repeating steps (a) and (b) using said progeny plant of the further subsequent generation from step (b) in place of the plant grown from said $F_1$ hybrid wheat seed in step (a), wherein steps (a) and (b) are repeated with sufficient inbreeding to produce an inbred wheat plant derived from the wheat variety OK15MASBx7 ARS 8-29.

21. A method of introducing a desired trait into wheat variety OK15MASBx7 ARS 8-29 comprising: (a) crossing the wheat variety OK15MASBx7 ARS 8-29 plant of claim 8 with another wheat plant that comprises a desired trait to produce $F_1$ progeny plants; (b) selecting one or more progeny plants that have the desired trait; (c) crossing the selected progeny plants with wheat variety OK15MASBx7 ARS 8-29 plants to produce backcross progeny plants; (d) selecting for backcross progeny plants that have the desired trait; and (e) repeating steps (c) and (d) three or more times in succession to produce selected fourth or higher backcross progeny plants that comprise the desired trait and essentially all of the physiological and morphological characteristics of wheat variety OK15MASBx7 ARS 8-29 when grown in the same environmental conditions as wheat variety OK15MASBx7 ARS 8-29.

22. A wheat plant or plant part produced by the method of claim 21, wherein the plant has the desired trait and otherwise all of the physiological and morphological characteristics of wheat variety OK15MASBx7 ARS 8-29.

23. A method of vegetatively propagating a plant of wheat variety OK15MASBx7 ARS 8-29, the method comprising:

a. collecting tissue capable of being propagated from the plant of claim 8;
b. cultivating the tissue to obtain proliferated shoots to obtain rooted plantlets; and
c. optionally growing plants from the rooted plantlets.

24. A plant or rooted plantlet as produced by the method of claim 23.

25. A method of producing a progeny wheat plant comprising applying plant breeding techniques to the plant of claim 8 to yield said progeny wheat plant.

26. The method of claim 25, wherein the plant breeding technique is one or more of backcrossing, marker assisted breeding, pedigree breeding, selfing, outcrossing, haploid production, doubled haploid production, or transformation.

27. A progeny wheat plant produced by the method of claim 26, wherein the progeny wheat plant is an $F_1$ wheat plant.

28. A method of producing a Hard Red Winter (HRW) wheat plant having increased dough strength, the method comprising crossing the plant of claim 1 with a second HRW wheat plant to produce a progeny HRW wheat plant, wherein the progeny HRW wheat plant has increased dough strength as compared to a typical HRW wheat variety.

29. The method of claim 7, wherein the commodity plant product is flour.

* * * * *